(12) United States Patent
Goldfarb et al.

(10) Patent No.: US 8,343,174 B2
(45) Date of Patent: Jan. 1, 2013

(54) LOCKING MECHANISMS FOR FIXATION DEVICES AND METHODS OF ENGAGING TISSUE

(75) Inventors: Eric A. Goldfarb, San Francisco, CA (US); Jaime E. Sarabia, San Jose, CA (US); Alfred H. Raschdorf, Kings Park, NY (US); John P. Madden, Redwood City, CA (US)

(73) Assignee: Evalve, Inc., Menlo Park, CA (US)

( * ) Notice: Subject to any disclaimer, the term of this patent is extended or adjusted under 35 U.S.C. 154(b) by 789 days.

(21) Appl. No.: 12/554,162

(22) Filed: Sep. 4, 2009

(65) Prior Publication Data
US 2009/0326567 A1    Dec. 31, 2009

Related U.S. Application Data

(60) Division of application No. 11/130,818, filed on May 16, 2005, now Pat. No. 7,604,646, and a continuation-in-part of application No. 10/441,531, filed on May 19, 2003, now Pat. No. 7,563,267, which is a continuation-in-part of application No. 09/894,463, filed on Jun. 27, 2001, now Pat. No. 6,752,813, which is a continuation-in-part of application No. 09/544,930, filed on Apr. 7, 2000, now Pat. No. 6,629,534.

(60) Provisional application No. 60/571,217, filed on May 14, 2004, provisional application No. 60/128,690, filed on Apr. 9, 1999.

(51) Int. Cl.
*A61B 17/08* (2006.01)
(52) U.S. Cl. .......................... 606/151; 606/213
(58) Field of Classification Search .................. 606/151, 606/213, 232; 623/2.12
See application file for complete search history.

(56) References Cited

U.S. PATENT DOCUMENTS
2,108,206 A    2/1938    Meeker
(Continued)

FOREIGN PATENT DOCUMENTS
DE          3504292          7/1986
(Continued)

OTHER PUBLICATIONS

International Search Report and Written Opinion of PCT Application No. PCT/US2009/068023, mailed Mar. 2, 2010, 11 pages total.

(Continued)

*Primary Examiner* — Corrine M McDermott
*Assistant Examiner* — Gregory Anderson
(74) *Attorney, Agent, or Firm* — Sughrue Mion, PLLC; Jonathan Feuchtwang

(57) ABSTRACT

Devices and methods are provided for tissue approximation and repair. Fixation devices comprise a pair of elements each having a first end, a free end opposite the first end, and an engagement surface therebetween for engaging the tissue, the first ends being moveable between an open position wherein the free ends are spaced apart and a closed position wherein the free ends are closer together with the engagement surfaces generally facing each other. The fixation devices include a locking mechanism coupled to the elements for locking the elements in place. The devices and methods find use in a variety of therapeutic procedures, including endovascular, minimally-invasive, and open surgical procedures, and can be used in various anatomical regions. The invention is particularly useful in procedures requiring minimally-invasive or endovascular access to remote tissue locations, where the instruments utilized must negotiate long, narrow, and tortuous pathways to the treatment site.

24 Claims, 23 Drawing Sheets

U.S. PATENT DOCUMENTS

| | | |
|---|---|---|
| 3,296,668 A | 1/1967 | Aiken |
| 3,378,010 A | 4/1968 | Codling |
| 3,671,979 A | 6/1972 | Moulopoulos |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,112,951 A | 9/1978 | Hulka et al. |
| 4,235,238 A | 11/1980 | Ogiu et al. |
| 4,297,749 A | 11/1981 | Davis et al. |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,350,397 A | 9/1994 | Palermo et al. |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,383,886 A | 1/1995 | Kensey et al. |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,507,725 A | 4/1996 | Savage et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 2,097,018 A | 10/1997 | Chamberlain |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keital et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |

| Patent | Date | Inventor |
|---|---|---|
| 5,836,955 A | 11/1998 | Buelna et al. |
| 5,840,081 A | 11/1998 | Andersen et al. |
| 5,843,031 A | 12/1998 | Hermann et al. |
| 5,849,019 A | 12/1998 | Yoon |
| 5,853,422 A | 12/1998 | Huebsch et al. |
| 5,855,271 A | 1/1999 | Eubanks et al. |
| 5,855,614 A | 1/1999 | Stevens et al. |
| 5,860,990 A | 1/1999 | Nobles et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhardt et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Séguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |

| | | |
|---|---|---|
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055774 A1 | 5/2002 | Liddicoat |
| 2002/0055775 A1 | 5/2002 | Carpentier et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183835 A1 | 12/2002 | Taylor et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0088047 A1 | 5/2004 | Spence et al. |
| 2004/0092962 A1 | 5/2004 | Thorton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goar et al. |
| 2005/0021057 A1 | 1/2005 | St. Goar et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Rahdert et al. |
| 2007/0038293 A1 | 2/2007 | St.Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thornton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goar et al. |
| 2008/0183194 A1 | 7/2008 | Goldfarb et al. |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2010/0016958 A1 | 1/2010 | St. Goar et al. |
| 2010/0022823 A1 | 1/2010 | Goldfarb et al. |

FOREIGN PATENT DOCUMENTS

| | | |
|---|---|---|
| EP | 0 179 562 A1 | 4/1986 |
| EP | 0 179 562 B1 | 7/1989 |
| EP | 0 558 031 | 2/1993 |
| EP | 0 684 012 | 11/1995 |

| | | |
|---|---|---|
| EP | 0 727 239 | 8/1996 |
| EP | 1 674 040 | 6/2006 |
| FR | 2151142 | 7/1985 |
| FR | 2768324 | 3/1999 |
| GB | 1598111 | 9/1981 |
| JP | 59-85653 A | 5/1984 |
| JP | 11-089937 | 4/1999 |
| JP | 2000-283130 A | 10/2000 |
| WO | WO 81/00668 | 3/1981 |
| WO | WO 91/01689 | 2/1991 |
| WO | WO 92/12690 | 8/1992 |
| WO | WO 94/18881 | 9/1994 |
| WO | WO 94/18893 | 9/1994 |
| WO | WO 95/15715 A1 | 6/1995 |
| WO | WO 96/14032 A1 | 5/1996 |
| WO | WO 96/22735 | 8/1996 |
| WO | WO 96/30072 A1 | 10/1996 |
| WO | WO 97/25927 A1 | 7/1997 |
| WO | WO 97/26034 A1 | 7/1997 |
| WO | WO 97/38748 A2 | 10/1997 |
| WO | WO 97/39688 | 10/1997 |
| WO | WO 97/48436 A2 | 12/1997 |
| WO | WO 98/07375 | 2/1998 |
| WO | WO 98/24372 | 6/1998 |
| WO | WO 98/30153 | 7/1998 |
| WO | WO 98/32382 | 7/1998 |
| WO | WO 98/35638 | 8/1998 |
| WO | WO 99/00059 | 1/1999 |
| WO | WO 99/07354 | 2/1999 |
| WO | WO 99/13777 A1 | 3/1999 |
| WO | WO 99/66967 A1 | 12/1999 |
| WO | WO 00/02489 | 1/2000 |
| WO | WO 00/03651 A1 | 1/2000 |
| WO | WO 00/03759 | 1/2000 |
| WO | WO 00/12168 A1 | 3/2000 |
| WO | WO 00/44313 A1 | 8/2000 |
| WO | WO 00/59382 | 10/2000 |
| WO | WO 00/60995 | 10/2000 |
| WO | WO 01/00111 | 1/2001 |
| WO | WO 01/00114 A1 | 1/2001 |
| WO | WO 01/03651 A2 | 1/2001 |
| WO | WO 01/26557 | 4/2001 |
| WO | WO 01/26586 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 | 4/2001 |
| WO | WO 01/28455 | 4/2001 |
| WO | WO 01/47438 A1 | 7/2001 |
| WO | WO 01/49213 A2 | 7/2001 |
| WO | WO 01/49213 A3 | 7/2001 |
| WO | WO 01/50985 A1 | 7/2001 |
| WO | WO 01/54618 | 8/2001 |
| WO | WO 01/56512 A1 | 8/2001 |
| WO | WO 01/66001 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 | 1/2002 |
| WO | WO 02/34167 A2 | 5/2002 |
| WO | WO 02/34167 A3 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 | 1/2003 |
| WO | WO 03/003930 A1 | 1/2003 |
| WO | WO 03/020179 | 3/2003 |
| WO | WO 03/028558 | 4/2003 |
| WO | WO 03/037171 | 5/2003 |
| WO | WO 03/047467 | 6/2003 |
| WO | WO 03/049619 | 6/2003 |
| WO | WO 03/073910 | 9/2003 |
| WO | WO 03/073913 | 9/2003 |
| WO | WO 03/105667 | 12/2003 |
| WO | WO 2004/004607 | 1/2004 |
| WO | WO 2004/012583 | 2/2004 |
| WO | WO 2004/012789 A2 | 2/2004 |
| WO | WO 2004/014282 A2 | 2/2004 |
| WO | WO 2004/019811 | 3/2004 |
| WO | WO 2004/030570 | 4/2004 |
| WO | WO 2004/037317 | 5/2004 |
| WO | WO 2004/045370 | 6/2004 |
| WO | WO 2004/045378 | 6/2004 |
| WO | WO 2004/045463 | 6/2004 |
| WO | WO 2004/047679 | 6/2004 |
| WO | WO 2004/062725 | 7/2004 |
| WO | WO 2004/082523 | 9/2004 |
| WO | WO 2004/082538 | 9/2004 |
| WO | WO 2004/093730 | 11/2004 |
| WO | WO 2004/112585 | 12/2004 |
| WO | WO 2004/112651 | 12/2004 |
| WO | WO 2005/002424 | 1/2005 |
| WO | WO 2005/018507 | 3/2005 |
| WO | WO 2005/027797 | 3/2005 |
| WO | WO 2005/032421 | 4/2005 |
| WO | WO 2005/062931 | 7/2005 |
| WO | WO 2005/112792 | 12/2005 |
| WO | WO 2006/105008 | 10/2006 |
| WO | WO 2006/105009 | 10/2006 |
| WO | WO 2006/115875 | 11/2006 |
| WO | WO 2006/115876 | 11/2006 |

OTHER PUBLICATIONS

Abe et al., "De Vega's annuloplasty for acquired tricuspid disease: Early and late results in 110 patients" Ann. Thorac. Surg. (1989) 48:670-676.

Abe et al., "Updated: De Vega's annuloplasty for acquired tricuspid disease: Early and late results in 110 patients" Ann. Thorac. Surg. (1996) 62:1876-1877.

Agricola et al., "Mitral valve reserve in double orifice technique: an exercise echocardiographic study," Journal of Heart Valve Disease, (2002)11(5):637 643.

Alfieri, et al., "An effective technique to correct anterior mitral leaflet prolapse," J Card Surg, 1999; 14(6):468-470.

Alfieri et al., "Novel suture device for beating heart mitral leaflet approximation," Annals of Thoracic Surgery, (2002)74:1488 1493.

Alfieri et al., "The double orifice technique in mitral valve repair: a simple solution for complex problems," Journal of Thoracic Cardio-vascular Surgery, (2001)122:674 681.

Alfieri et al., "The edge to edge technique," The European Association for Cardio-Thoracic Surgry 14th Annual Meeting, Oct. 7-11, 2000, Book of Proceedings.

Alfieri , "The edge-to-edge repair of the mitral valve," [Abstract] 6th Annual NewEra Cardiac Care: Innovation & Technology, Heart Surgery Forum, (2003) pp. 103.

Alvarez et al., "Repairing the degenerative mitral valve: Ten- to fifteen-year follow-up" J. Thorac. Cardiovasc. Surg. (1996) 112:238-247.

Arisi et al., "Mitral valve repair with Alfieri technique in mitral regurgitation of diverse etiology: early echocardiographic results," Circulation Supplement II, (2001) 104(17):3240.

Bach et al., "Early improvement in congestive heart failure after correction of secondary mitral regurgitation in end-stage cardiomyopathy," Am. Heart J., (1995) 129:1165-1170.

Bach et al., "Improvement following correction of secondary mitral regurgitation in end-stage cardiomyopathy with mitral annuloplasty" Am. J. Cardiol., (1996) 78:966-969.

Bailey, "Surgery of the Heart," Chapter 20, (1955) pp. 686-737.

Bernal et al., "The 'Valve Racket': a new and different concept of atrioventricular valve repair," Eur. J. Cardio-thoracic Surgery 29:1026-29 (2006).

Bhudia, #58 Edge-to-edge mitral repair: a versatile mitral repair technique, 2003 STS Presentation, [Abstract Only].

Bhudia et al., "Edge-to-edge (Alfieri) mitral repair: results in diverse clinical settings," Ann Thorac Surg, 77: 1598-1606, (2004).

Bollling et al., "Surgery for acquired heart disease," (1995) 109:676-683.

Borghetti et al., "Preliminary observations on haemodynamics during physiological stress conditions following 'double-orifice' mitral valve repair," European Journal of Cardio-thoracic Surgery, Apr. 18, 2001 20:262-269.

Castedo, "Edge-to-edge tricuspid repair for redeveloped valve incompetence after DeVega's annuloplasty," AnnThora Surg, (2003) 75;605-6.

Dec et al., "Idiopathic dilated cardiomyopathy," N. Engl. J. Med., (1994) 331:1564-1575.

Dottori et al., "Echocardiographic imaging of the Alfieri type mitral valve repair," Ital Heart J, (2001) 2(4):319-320.

Downing et al., "Beating heart mitral valve surgery: Preliminary model and methodology," Journal of Thoracic and Cardiovascular Surgery, (2002) 123(6):1141-1146.

Falk et al., "Computer-enhanced mitral valve surgery: toward a total endoscopic procedure," Seminars in thoracic and cardiovascular surgery, (1999) 11(3):224-249.

Filsoufi et al., "Restoring Optimal Surface of Coaptation With a Mini Leaflet Prosthesis: A New Surgical Concept for the Correction of Mitral Valve Prolapse," Int'l. Soc. for Minimally Invasive Cardiothoracic Surgery 1(4):186-87 (2006).

Frazier et al., #62 Early Clinical Experience With an Implantable, Intracardiac Circulatory Support Device: Operative Considerations and Physiologic Implications, 2003 STS Presentation, 1 page total. [Abstract Only].

Fucci et al., "Improved results with mitral valve repair using new surgical techniques" Eur. J. Cardiothorac Sug. (1995) 9:621-627 (Medline Record enclosed herewith.).

Fundaro et al., "Chordal plication and free edge remodeling for mitral anterior leaflet prolapse repair: 8-year follow-up," Annals of Thoracic Surgery, (2001) 72:1515-1519.

Garcia-Rinaldi et al., "Left ventricular volume reduction and reconstruction is ischemic cardiomyopathy," Journal of Cardiac Surgery, (1999) 14:199-210.

Gateliene, "Early and postoperative results of metal and tricuspid valve insufficiency surgical treatment using edge-to-edge central coaptation procedure," (2002) 38 Suppl 2:172-5.

Gatti et al., "The edge to edge technique as a trick to rescue an imperfect mitral valve repair," Eur J Cardiothorac Surg, (2002) 22(5):817 20.

Gillinov et al., "Is minimally invasive heart valve surgery a paradigm for the future?," Current Cardiology Reports, (1999) 1:318-322.

Gundry, "Facile mitral valve repair utilizing leaflet edge approximation: midterm results of the Alfieri figure of eight repair," Presented at the Meeting of the Western Thoracic Surgical Association, (1999).

Gupta et al., #61 Influence of Older Donor Grafts on Heart Transplant Survival: Lack of Recipient Effects, 2003 STS Presentation, [Abstract Only].

Ikeda et al., "Batista's operation with coronary artery bypass grafting and mitral valve plasty for ischemic dilated cardiomyopathy," The Japanese Journal of Cardiac and Cardiovascular Surgery, (2000) 48:746-749.

Izzat et al., "Early experience with partial left ventriculectomy in the Asia-Pacific Region," Annals of Thoracic Surgery, (1999) 67:1703-1707.

Källner et al., "Transaortic approach for the Alfieri Stitch," Ann Thorac Surg, 2001; 71:378-380.

Kameda et al., "Annuloplasty for severe mitral regurgitation due to dilated cardiomyopathy," Am. Thorac. Surg, (1996) 61:1829-1832.

Kavarna et al., "Transaortic repair of mitral regurgitation," Presented at the third annual New Era Cardiac Care conference, San Diego, CA, Jan. 13-16, 2000, http://www.hsforum.com/vol3/issue1/2000-2389print.html.

Kaza et al., "Ventricular reconstruction results in improved left ventricular function and amelioration of mitral insufficiency," Annals of Surgery, (2002) 235(6):828 832.

Khan et al., "Blade atrial septostomy: Experience with the first 50 procedures" Cathet. Cardiovasc. Diagn, (1991) 23:257-262.

Kherani et al., "Edge-to-edge mitral valve repair: the Columbia Presbyterian experience," Ann Thorac Surg, 2004; 78: 73-76.

Konertz et al., "Results after partial left ventriculectomy in a European heart failure population," J. Cardiac Surg, 1999; 14(2):129-135.

Kron et al., "Surgical relocation of the posterior papillary muscle in chronic ischemic mitral regurgitation," Annals. of Thoracic Surgery, (2002)74:600 601.

Krüger et al, "Edge to edge technique in complex mitral valve repair," Thorac Cardiovasc Surg, 2000, Thema: Poster, http://www.thieme.de/thoracic/abstracts/abstracts/$p_{13}$73.html.

Langer et al., "Posterior mitral leaflet extensions: An adjunctive repair option for ischemic mitral regurgitation?," J. Thorac. Cardiovasc. Surf. 131:868-77 (2006).

Lorusso e al., "Double-Orifice technique to repair extensive mitral valve excision following acute endocarditis," J Card Surg, 1998; 13:24-26.

Lorusso et al., "The double-orifice technique for mitral valve construction: predictors of postoperative outcome," Eur J. Cardiothorac Surg, May 23, 2001; 20(3):583-589.

Maisano et al., "The double orifice repair for Barlow Disease: a simple solution for a complex repair," Supplement I Circulation, 1999; 100(18):1-94.

Maisano et al., "The double orifice technique as a standardized approach to treat mitral regurgitation due to severe myxomatous disease: surgical technique," Eur J. Cardiothoracic Surg., Jan. 18, 2000; 17:201-215.

Maisano et al., "The hemodynamic effects of double-orifice valve repair for mitral regurgitation: a 3D computational model," European Journal of Cardio-thoracic Surgery, 1999; 15:419-425.

Maisano et al., "Valve repair for traumatic tricuspid regurgitation," Eur J. Cardio-Thorac Surg, 1996; 10:867-873.

Maisano et al., "The edge-to-edge technique: a simplified method to correct mitral insufficiency" Eur. J. Cardiothorac. Surg., (1998) 13:240-246.

Mantovani et al., "Edge-to-edge repair of congenital familiar tricuspid regurgitation: case report," J. Heart Valve Dis, Sep. 2000; 9 (5):641-643.

McCarthy et al. "Tricuspid valve repair with the Cosgrove-Edwards annuloplasty system" Am. Thorac. Surg., (1997) 64:267-268.

McCarthy et al., "Partial left ventriculectomy and mitral valve repair for end-stage congestive heart failure," Eur J. Cardio-thoracic Surgery, 1998; 13:337-343.

Moainie et al., Correction of traumatic tricuspid regurgitation using the double orifice technique, Annals of Thoracic Surgery, (2002) 73:963 965.

Morales et al., "Development of an off bypass mitral valve repair," The Heart Surgery Forum #1999-4963, (1999) 2(2):115-120.

Nakanishi et al., "Early outcome with the Alfieri mitral valve repair," J Cardiol, May 2001; 37(5):263-266, (Abstract in English; Article in Japanese.).

Nielsen et al., "The edge-to-edge mitral repair: tension on the approximating suture and leaflet deformation during acute ischemic mitral regurgitation in the ovine heart," Circulation, 2001;104 [ suppl I]:I-29-I-35.

Noera et al. ., "Tricuspid Valve Incompetence Caused by Nonpenetrating Thoracic Trauma", Annals of Thoracic Surgery, 1991, 51 (2), 320-322.

Osawa et al., "Partial left ventriculectomy in a 3 year old boy with dilated cardiomyopathy," Japanese Journal of Thoracic and Cardiovascular Surg, Sep. 2000, 48(9):590-593.

Park et al., "Clinical use of a blade atrial septostomy" Circulation (1978) 58:600-608.

Patel et al., #57 Epicardial Atrial Defibrillation: Novel Treatment of Postoperative Atrial Fibrillation, 2003 STS Presentation, [Abstract Only] .

Privitera et al., "Mitral Valve Repair: Clinical Outcome and Pathology; Circulation," (2002) 106:173.

Redaelli et al., A computational study of the hemodynamics after 'edge-to-edge' mitral valve repair, Journal of Biomechanical Engineering, (2001) 123:565-570.

Reul et al., "Mital valve reconstruction for mitral insufficiency," Progress in Cardiovascular Diseases, (1997) vol. XXXIX, No. 6, pp. 567-599.

Ricchi et al., "Linear segmental annuloplasty for mitral valve repair" Ann. Thorac. Surg., (1997) 63:1805-1806.

Robicsek et al., #60 The Bicuspid Aortic Valve: How Does It Function? Why Does It Fail?, 2003 STS Presentation, [Abstract Only].

Tager et al., "Long-term follow-up of Rheumatic patients undergoing left-sided valve replacement with tricuspid annuloplasty—Validity of preoperative echocardiographic criteria in the decision to perform tricuspid annulopasty" Am. J. Cardiol., (1998) 81:1013-1016.

Tamura et al., Edge to edge repair for mitral regurgitation in a patient with chronic hemodialysis: report of a case, Kyobu Geka, (2001) 54(9):788-790.

Tibayan et al., #59 Annular Geometric Remodeling in Chronic Ischemic Mitral Regurgitation, 2003 STS Presentation, [Abstract Only].

Timek et al., "Edge-to-edge mitral repair: gradients and three-dimensional annular dynamics in vivo during inotropic stimulation," Eur J. of Cardiothoracic Surg., Jan. 9, 2001; 19:431-437.

Timek, "Edge-to-edge mitral valve repair without annuloplasty ring in acute ischemic mitral regurgitation," [Abstract] Clinical Science, Abstracts from Scientific Sessions, (2002) II-461.

Totaro et al., "Mitral valve repair for isolated prolapse of the anterior leaflet: an 11 year follow-up," Eur J. Cardio-Thoracic Surg, 1999; 15:119-126.

Uchida et al., "Percutaneous cardiomyotomy and valvultomy with angioscopic guidance," Am. Heart J., (1991) 121:1221-1224.

Umana et al., "'Bow-tie' mitral valve repair successfully addresses subvalvular dysfunction in ischemic mitral regurgitation," (1997) Surgical Forum pp. 279-280.

Umana, "'Bow-Tie' mitral valve repair: an adjuvant technique for ischemic mitral regurgitation," AnnThora Surg, (1998) 66:1640-6.

Votta et al., "3 D computational analysis of the stress distribution on the leaflets after edge to edge repair of mitral regurgitation," Journal of Heart Valve Disease, (2002)11:810 822.

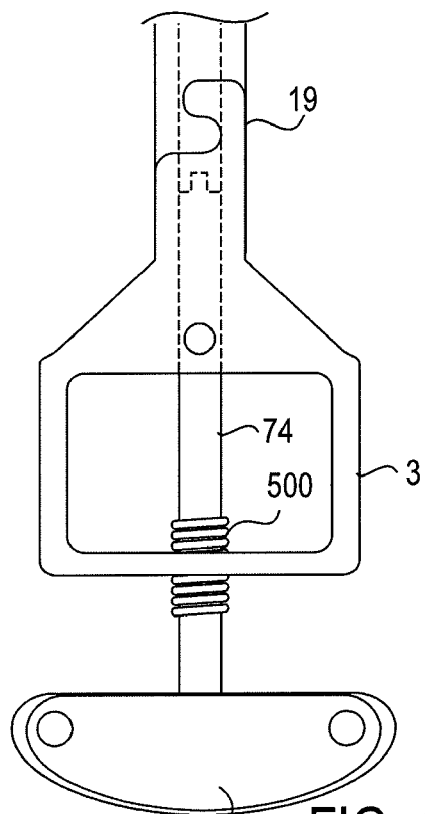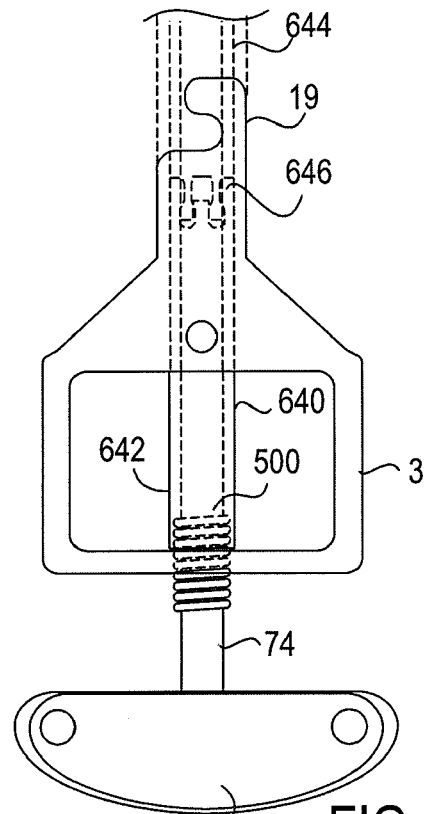
FIG. 14A
FIG. 14B
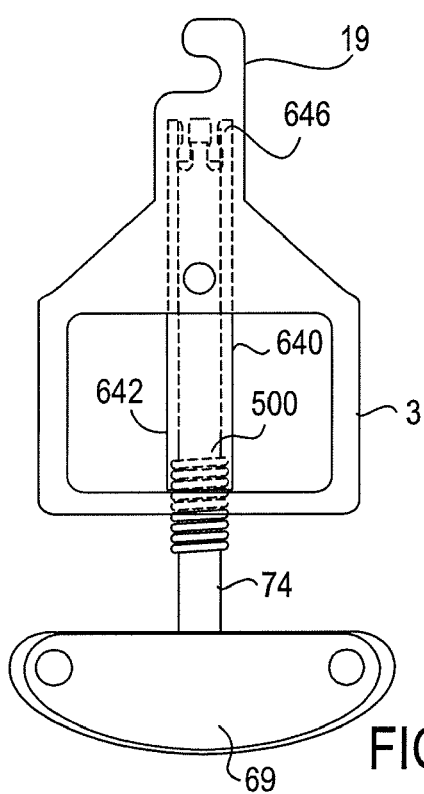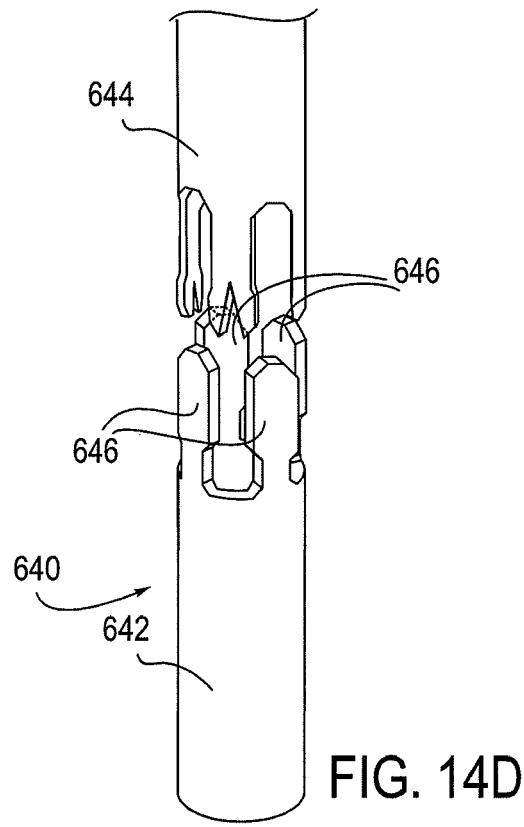
FIG. 14C
FIG. 14D

LOCKING MECHANISMS FOR FIXATION DEVICES AND METHODS OF ENGAGING TISSUE

CROSS-REFERENCES TO RELATED APPLICATIONS

The present application is a divisional of U.S. patent application Ser. No. 11/130,818, now U.S. Pat. No. 7,604,646, filed May 16, 2005, which claims the benefit and priority of U.S. Provisional Patent Application No. 60/571,217, filed May 14, 2004, and is a continuation-in-part of U.S. patent application Ser. No. 10/441,531, now U.S. Pat. No. 7,563,267, filed May 19, 2003 which is a continuation-in-part of, and claims the benefit of priority from U.S. patent application Ser. No. 09/894,463 now U.S. Pat. No. 6,752,813, filed Jun. 27, 2001, which is a continuation-in-part of U.S. patent application Ser. No. 09/544,930 now U.S. Pat. No. 6,629,534, filed Apr. 7, 2000, which claims the benefit of prior Provisional Application No. 60/128,690, filed on Apr. 9, 1999 under 37 CFR §1.78(a), the full disclosures of which are hereby incorporated herein by reference.

In addition, U.S. patent application Ser. No. 10/441,531 is related to U.S. patent application Ser. No. 10/441,753, U.S. patent application Ser. No. 10/441,508, and U.S. patent application Ser. No. 10/441,687, all of which were filed on the same day (May 19, 2003), the full disclosures of which are incorporated herein by reference.

BACKGROUND OF THE INVENTION

1. Field of the Invention

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

For these reasons, it would be desirable to provide alternative and additional methods, devices, and systems for performing the repair of mitral and other cardiac valves. Such methods, devices, and systems should preferably not require open chest access and be capable of being performed either endovascularly, i.e., using devices which are advanced to the heart from a point in the patient's vasculature remote from the heart or by a minimally invasive approach. Further, such devices and systems should provide features which allow repositioning and optional removal of a fixation device prior to fixation to ensure optimal placement. Still further, the fixation devices should be able to be locked in a fixed position and left behind for implantation. Still more preferably, the methods, devices, and systems would be useful for repair of tissues in the body other than heart valves. At least some of these objectives will be met by the inventions described hereinbelow.

2. Description of the Background Art

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759.

Maisano et al. (1998) *Eur. J. Cardiothorac. Surg.* 13:240-246; Fucci et al. (1995) *Eur. J. Cardiothorac. Surg.* 9:621-627; and Umana et al. (1998) *Ann. Thorac. Surg.* 66:1640-1646, describe open surgical procedures for performing "edge-to-edge" or "bow-tie" mitral valve repair where edges of the opposed valve leaflets are sutured together to lessen regurgitation. Dec and Fuster (1994) *N. Engl. J. Med.* 331:1564-1575 and Alvarez et al. (1996) *J. Thorac. Cardiovasc. Surg.* 112:238-247 are review articles discussing the nature of and treatments for dilated cardiomyopathy.

Mitral valve annuloplasty is described in the following publications. Bach and Bolling (1996) *Am. J. Cardiol.* 78:966-969; Kameda et al. (1996) *Ann. Thorac. Surg.* 61:1829-1832; Bach and Bolling (1995) *Am. Heart J.* 129:1165-1170; and Bolling et al. (1995) 109:676-683. Linear segmental annuloplasty for mitral valve repair is described in Ricchi et al. (1997) *Ann. Thorac. Surg.* 63:1805-1806. Tricuspid valve annuloplasty is described in McCarthy and Cosgrove (1997) *Ann. Thorac. Surg.* 64:267-268; Tager et al. (1998) *Am. J. Cardiol.* 81:1013-1016; and Abe et al. (1989) *Ann. Thorac. Surg.* 48:670-676.

Percutaneous transluminal cardiac repair procedures are described in Park et al. (1978) *Circulation* 58:600-608; Uchida et al. (1991) *Am. Heart J.* 121: 1221-1224; and Ali Khan et al. (1991) *Cathet. Cardiovasc. Diagn.* 23:257-262.

Endovascular cardiac valve replacement is described in U.S. Pat. Nos. 5,840,081; 5,411,552; 5,554,185; 5,332,402; 4,994,077; and 4,056,854. See also U.S. Pat. No. 3,671,979 which describes a catheter for temporary placement of an artificial heart valve.

Other percutaneous and endovascular cardiac repair procedures are described in U.S. Pat. Nos. 4,917,089; 4,484,579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

BRIEF SUMMARY OF THE INVENTION

The invention provides devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations, where the instruments utilized must negotiate long, narrow, and tortuous pathways to the treatment site. In addition, many of the devices and systems of the invention are adapted to be repositionable or reversible and removable from the patient at any point without interference with or trauma to internal tissues.

In preferred embodiments, the devices, systems and methods of the invention are adapted for fixation of tissue at a treatment site. Exemplary tissue fixation applications include cardiac valve repair, septal defect repair, patent foramen ovale repair, vascular ligation and clamping, laceration repair and wound closure, but the invention may find use in a wide variety of tissue approximation and repair procedures. In a particularly preferred embodiment, the devices, systems and methods of the invention are adapted for repair of cardiac valves, and particularly the mitral valve, as a therapy for regurgitation. The invention enables two or more valve leaflets to be coapted using an "edge-to-edge" or "bow-tie" technique to reduce regurgitation, yet does not require open surgery through the chest and heart wall as in conventional approaches.

Using the devices, systems and methods of the invention, the mitral valve can be accessed from a remote surgical or vascular access point and the two valve leaflets may be coapted and fixed together using endovascular or minimally invasive approaches. The devices of the present invention include a fixation device having a locking mechanism which allows the user to "lock" the fixation devices in a desired position to fix the leaflets together. In some embodiments, the locking mechanism locks the fixation device in a single predetermined configuration or in one of a few predetermined configurations. In other embodiments, the locking mechanism allows locking at any point along a continuum of points on the device so that the user may choose the desired position for fixing the leaflets together during the procedure. The desired position for fixing the leaflets may vary due to variability in the thickness and amount of tissue captured by the fixation device, the presence or absence of disease (e.g. calcification, hypertrophy), the age of the patient and other factors potentially unknown to the user prior to the procedure. For example, if more tissue is captured or coapted by the fixation device, the fixation device may not be able to close as far than if less tissue is captured. Therefore, in some circumstances it may be advantageous that the locking mechanism of the fixation device be lockable at a specific, non-predetermined point desired by the user even though that point may not be able to be determined prior to the procedure.

In some circumstances the invention may also find application in open surgical approaches as well. According to the invention, the mitral valve may be approached either from the atrial side (antegrade approach) or the ventricular side (retrograde approach), and either through blood vessels or through the heart wall.

In a first aspect of the present invention, a fixation device is provided having a pair of distal elements (or fixation elements), each distal element having a free end and an engagement surface for engaging the tissue, wherein the distal elements are moveable between a first position for capturing the tissue and a second position for fixing the tissue. Preferably, the engagement surfaces are spaced apart in the first position and are closer together and generally face toward each other in the second position. The fixation device is preferably delivered to a target location in a patient's body by a delivery catheter having an elongated shaft, a proximal end and a distal end, the delivery catheter being configured to be positioned at the target location from a remote access point such as a vascular puncture or cut-down or a surgical penetration. In a preferred embodiment, the target location is a valve in the heart.

In a second aspect of the present invention, the fixation device further includes a locking mechanism that maintains the distal elements in a selected position relative to each other. While a variety of locking mechanisms may be used. In some embodiments, the fixation device includes a moveable stud coupled to the fixation elements wherein movement of the stud moves the fixation elements between the positions. In such embodiments, the locking mechanism may comprise an engagement element engageable with the moveable stud wherein engagement restricts movement of the stud. In some instances, the engagement element comprises at least one wedging element which frictionally engages the moveable stud to restrict movement of the stud. In other embodiments, the engagement element has at least one protrusion which mates with at least one external groove on the stud so as to restrict movement of the stud.

Alternatively, the locking mechanism may comprises an interference element which is positionable along the moveable stud so that the interference element prevents movement of the moveable stud in at least a first direction by contacting a stationary surface of the fixation device. In some embodiments, the interference element comprises a locking sheath advanceable over the moveable stud so that the locking sheath prevents movement of the stud in the at least first direction by abutting against the stationary surface. In other embodiments, the moveable stud includes external grooves and the interference element comprises a lock nut mateable with the external grooves of the moveable stud so that the mated lock nut prevents movement of the stud in at least the first direction by abutting against the stationary surface.

It may be appreciated that the moveable stud may be comprised of a rigid material, such as a metal or plastic, or the moveable stud may be comprised of a flexible line, such as a suture. When the moveable stud comprises a flexible line, the locking mechanism may comprise an interference element which is positionable along the flexible line so that the interference element prevents movement of the flexible line in at least a first direction by contacting a stationary surface of the fixation device.

In still other embodiments, the locking mechanism comprises gears, wherein movement of the gears moves the fixation elements between the positions while locking the fixation elements in place at each position.

Further, in other embodiments, the locking mechanism comprises a biasing member which biases the fixation elements toward one of the positions. The biasing member may comprise a pair of spring loaded support sleeves positionable against a portion of the fixation device so as to bias the fixation elements toward one of the positions. Or, the biasing member may comprise a cinching band positionable around the fixation elements so as to bias the fixation elements toward one of the positions. In some embodiments, the cinching band comprises an elastic cinching band positionable around the fixation elements in a stretched configuration so as to apply biasing force to the fixation elements. In other embodiments, the cinching band comprises a cinching line positionable around the fixation elements in a lasso configuration so as to apply biasing force to the fixation elements when tightened.

Typically, the fixation further comprises at least one leg joined with the fixation elements so that movement of the at least one leg moves the fixation elements between the positions. In such embodiments, the at least one leg may have a spring loaded configuration so as to bias the fixation elements toward one of the positions. Alternatively or in addition, the locking mechanism may comprise a structure joinable with the at least one leg so as to prevent movement of the fixation elements. In some embodiments, the structure comprises a barb engagable with the at least one leg.

In a third aspect of the present invention, the fixation devices include an unlocking mechanism for disengaging the locking mechanism. In some embodiments, the unlocking mechanism comprises a harness, the harness adapted to disengage or reduce engagement of an engaging element from the moveable stud. For example, the harness may reduce frictional engagement a wedging element against the moveable stud.

In other aspect of the present invention, a locking mechanism coupled to the fixation elements is provided for locking the fixation elements in place along a continuum of positions between the open position and the closed position. Again, the fixation device may include a moveable stud coupled to the fixation elements wherein movement of the stud moves the fixation elements between the positions. In such embodiments, the locking mechanism may comprise at least one wedging element for frictionally engaging the stud to restrict movement thereof. For example, the at least one wedging element may comprise a binding plate having a first end, a second end and a portion therebetween shaped to engage the stud, the binding plate positioned so that the portion is disposed near the stud. The portion shaped to engage the stud may at least partially surround the stud and the binding plate may be positioned so that the portion at least partially surrounds the stud. In some embodiments, the portion shaped to at least partially surround the stud comprises an aperture, wherein the binding plate is positioned so that the stud passes through the aperture. The locking mechanism may further comprise a spring which forces the aperture against the stud to restrict movement of the stud through the aperture.

In some embodiments, the at least one wedging element comprises at least one cam, the at least one cam pivotable to frictionally engage the stud to restrict movement thereof. The at least one cam may have an inward surface engageable with the stud and an outward surface connected with a spring which forces the inward surface against the stud to restrict movement of the stud. Embodiments including an unlocking mechanism for disengaging the locking mechanism, may include at least one actuator attached to a pivot point on each of the at least one cams, the at least one actuator adapted to pivot the at least one cam about its pivot point to reduce frictional engagement of the inner surface with the stud. Sometimes, the at least one cam comprises two cams, each cam disposed on opposite sides of the stud.

In another aspect of the present invention, a locking mechanism coupled to the fixation elements is provided for locking the fixation elements in a position which allows movement of the fixation elements within a sub-range of the range. For example, in embodiments having a moveable stud coupled to the fixation elements wherein movement of the stud moves the fixation elements between the positions within the range, the stud may have may have at least one external groove for engagement by at least one wedging element wherein the at least one external groove is sized to allow shifting of the at least one wedging element within the at least one external groove which allows movement of the fixation elements within the sub-range. In other embodiments having such a moveable stud, the locking mechanism comprises at least one wedging element for frictionally engaging the stud to restrict movement thereof. In some instances, the at least one wedging element comprises an at least partially flexible material wherein flexing of the material allows movement of the fixation elements within the sub-range. In other instances, the at least one wedging element comprises a binding plate having a first end, a second end and a portion therebetween shaped to at least partially surround the stud, the binding plate positioned so that the portion at least partially surrounds the stud. In some embodiments, the portion shaped to at least partially surround the stud comprises an aperture and the binding plate is positioned so that the stud passes through the aperture.

It may be appreciated that the fixation elements may be configured for engaging valve leaflets of a valve within a heart, and movement of the fixation elements within the sub-range is achievable by force caused by dynamic fluid flow through the valve.

In another aspect of the present invention, a locking mechanism is provided comprising a moveable stud coupled to a device, wherein movement of the stud actuates movement of a portion of a device to a desired position in a range from a first position to a second position, at least one element configured to engage the stud to restrict movement of the stud which locks the device in the desired position, and an unlocking mechanism configured to disengage the at least one element from the stud which allows movement of the stud. In some instances, the at least one element comprises a binding plate having a first end, a second end and a portion therebetween shaped to at least partially surround the stud, the binding plate positioned so that the portion at least partially surrounds the stud. The portion shaped to at least partially surround the stud may comprise an aperture, the binding plate positioned so that the stud passes through the aperture. In some embodiments, the locking mechanism further comprising a spring configured to force the aperture against the stud to restrict movement of the stud through the aperture. The unlocking mechanism may comprise a harness, the harness adapted to move the second end while the first end remains substantially stationary so as to reduce frictional engagement of the at least partially surrounding portion with the stud.

In some embodiments, the at least one element comprises at least one cam, the at least one cam pivotable to frictionally engage the stud to restrict movement thereof. The at least one cam may have an inward surface engageable with the stud and an outward surface connected with a spring which forces the inward surface against the stud to restrict movement of the stud. In some embodiments, the unlocking mechanism comprises at least one actuator attached to a pivot point on each of the at least one cams, the at least one actuator adapted to pivot the at least one cam about its pivot point to reduce frictional engagement of the inner surface with the stud.

In still other embodiments, the moveable stud may have at least one external groove for engagement with the at least one element to restrict movement of the stud. Thus, the at least one element may comprise at least one component having at least one protrusion which mates with the at least one external groove of the stud wherein the at least one component is moveable to engage the at least one protrusion with the at least one external groove of the stud to restrict movement of the stud. In many of these embodiments, the unlocking mechanism comprises a hinge component which moves the at least one component to disengage the at least one protrusion from the at least one external groove. It may be appreciated that the at least one external groove may comprise threads and the at least one component comprise a split nut.

The desired position typically includes any position between the first position and the second position. Likewise, the desired position may includes one of a series of predetermined positions between the first position and the second position.

In another aspect of the present invention, a lockable system is provided comprising a device having a portion which is moveable to a desired position, and a locking mechanism coupled to the device. The locking mechanism comprises a moveable stud configured so that movement of the stud actuates movement of the portion of the device to the desired position, at least one element configured to engage the stud to restrict movement of the stud which locks the device in the desired position, and an unlocking mechanism configured to disengage the at least one element from the stud which allows movement of the stud.

In some embodiments, the device comprises a catheter. The catheter may include at least one pullwire fixedly attached to the stud so that movement of the stud moves the at least one pullwire which actuates movement of the portion of the catheter to the desired position. In other embodiments, the device comprises a grasper. The grasper may include at least one pullwire fixedly attached to the stud so that movement of the stud moves the at least one pullwire which actuates movement of the portion of the grasper to the desired position. And, in still other embodiments, the device comprises a retractor.

As mentioned, the locking mechanism of the present invention may be employed in catheter shafts, retractors, or other medical instruments such as graspers or biopsy forceps, where it is desirable to lock a device in a particular position prior to, during, or following a medical procedure. Such procedures can include biopsies or ablation procedures, wherein it is desired to navigate and hold catheter position, and retrieval procedures (e.g. of polyps, foreign objects).

Other objects and advantages of the present invention will become apparent from the detailed description to follow, together with the accompanying drawings.

BRIEF DESCRIPTION OF THE DRAWINGS

FIGS. 14A-14D, 15A-15B illustrate an embodiment of a locking mechanism which works against biasing forces that advance the stud of the fixation device.

DETAILED DESCRIPTION OF THE INVENTION

The fixation devices of the present invention provide for grasping, approximating and fixating tissues such as valve leaflets to treat cardiac valve regurgitation, particularly mitral valve regurgitation. In preferred embodiments, the fixation devices provide features that allow repositioning and removal of the device if so desired. Such removal would allow the practitioner to reapproach the valve in a new manner if so desired. Once the tissue has been satisfactorily approximated, the grasped tissue is typically fixed in place by maintaining grasping with the fixation device which is left behind as an implant.

The fixation device is releasably attached to a shaft of an interventional tool at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

Figure 1:
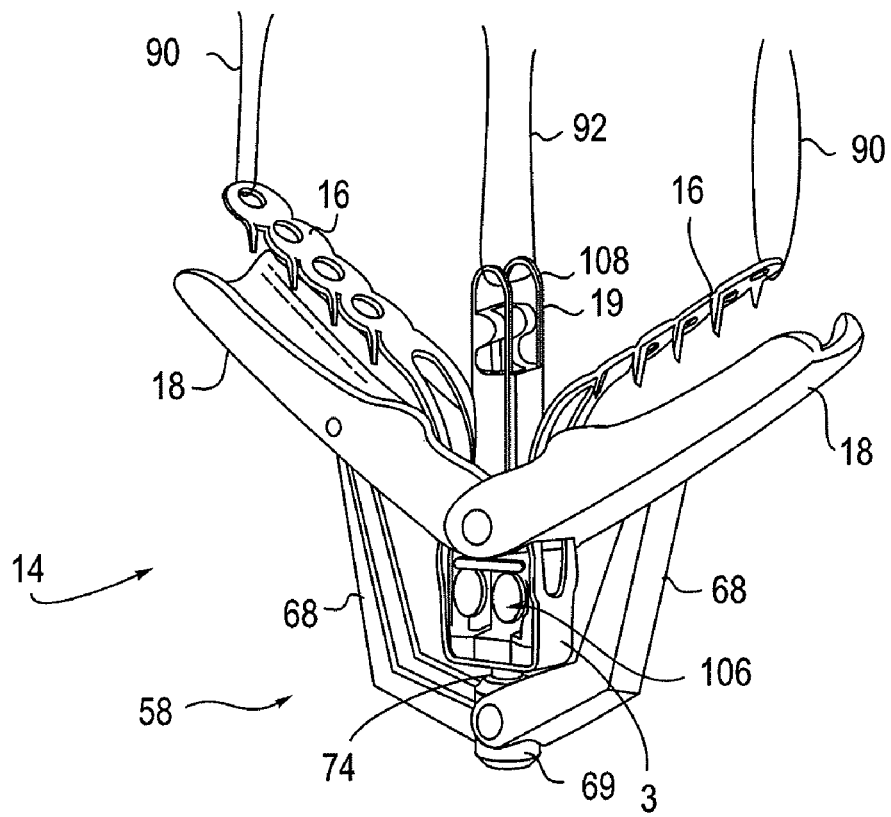
FIG. 1 illustrates an embodiment of a fixation device having an embodiment of a locking mechanism.

Referring to FIG. 1, a fixation device 14 typically comprises proximal elements 16 (or gripping elements) and distal elements 18 (or fixation elements) which protrude radially outward and are positionable on opposite sides of tissue, such as leaflets, so as to capture or retain the leaflets therebetween at a single location or along a continuum or range of positions as desired by the user. The fixation device 14 is coupleable to the shaft of the interventional tool (not shown) by a coupling mechanism, a portion of which is shown as coupling member 19. The coupling mechanism allows the fixation device 14 to detach and be left behind as an implant to hold the leaflets together in the coapted position. The coupling member 19 is either formed with or connected to housing 3 which typically houses locking mechanism 106.

Figure 2:
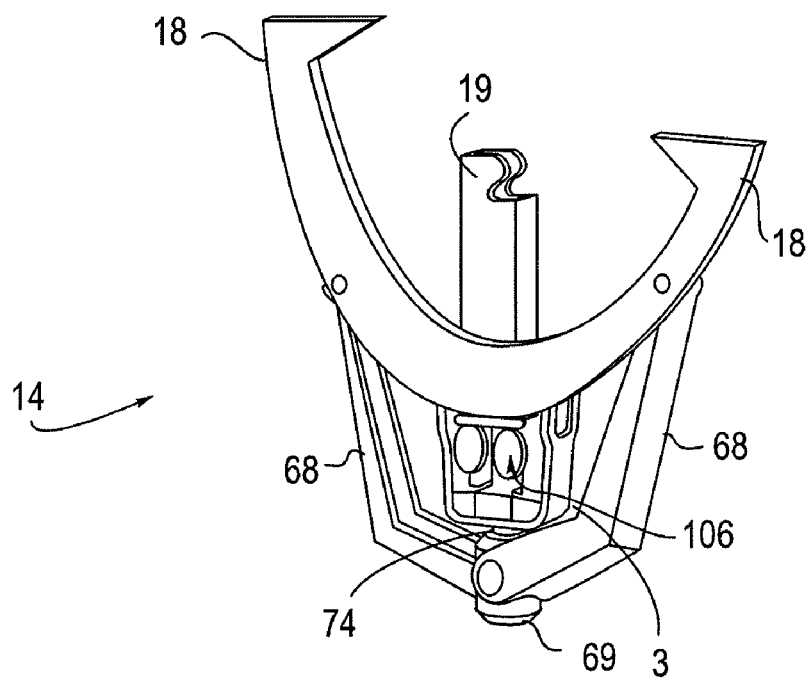
FIG. 2 illustrates another embodiment of a fixation device having an embodiment of a locking mechanism.

It may be appreciated that the fixation device 14 may have a variety of forms, of which FIG. 1 is an example. FIG. 2 illustrates another embodiment of a fixation device 14. Here, the fixation device 14 comprises distal elements 18 (or fixation elements) which protrude radially outward and are positionable on opposite sides of tissue, such as leaflets, so as to capture or retain the leaflets therebetween along a continuum as desired by the user. Here the distal elements 18 are formed from a continuous piece of material that is flexed to open and close by movement of the legs 68, however it may alternatively be hinged at the midpoint thereof. Again the fixation device 14 is coupleable to the shaft of the interventional tool (not shown) by a coupling mechanism, a portion of which is shown as coupling member 19. The coupling mechanism allows the fixation device 14 to detach and be left behind as an implant to hold the leaflets together in the coapted position.

In these embodiments, the fixation device 14 includes a locking mechanism for locking the device 14 in a particular position, such as an open, closed or inverted position or any position therebetween. It may be appreciated that the locking mechanism includes an unlocking mechanism which allows the device to be both locked and unlocked. FIGS. 1-3, 4A-4C illustrate an embodiment of a locking mechanism 106. Referring to FIG. 1, in this embodiment, the locking mechanism 106 is disposed between the coupling member 19 and the base 69 of the actuation mechanism 58. The base 69 is connected to the legs 68 of the actuation mechanism 58 which are in turn connected to the distal elements 18. Thus, movement of the legs 68 moves the distal elements 18 through open, closed and inverted positions. The base 69 is also fixedly attached to a stud 74 which extends through the locking mechanism 106. The stud 74 is releasably attached to an actuator rod which passes through the coupling member 19 and the shaft of the interventional tool. Release of the stud 74 from the actuator rod allows the fixation device 14 to be detached and left behind as an implant.

FIG. 1 also illustrates the proximal elements 16, which in this embodiment straddle the locking mechanism and join beneath the locking mechanism 106. The proximal elements 16 are shown supported by proximal element lines 90. The proximal elements 16 are raised and lowered by manipulation of the proximal element lines 90.

The proximal element lines 90 may be connected with the proximal elements 16 by threading the lines 90 in a variety of ways as described and illustrated in U.S. patent Ser. No. 10/441,531, incorporated herein by reference for all purposes. As described and illustrated, a line loop 48 may be present on a proximal element 16 through which a proximal element line 90 may pass and double back. Such a line loop 48 may be useful to reduce friction on proximal element line 90 or when the proximal elements 16 are solid or devoid of other loops or openings through which the proximal element lines 90 may attach. Line loops 48 may be comprised of any suitable material, may be formed into the proximal element 16 itself or may be formed from a material tied onto or attached to the proximal element 16. For example, the line loop 48 may be comprised of a suture loop which is tied to the proximal element 16, such as through an opening in the proximal element 16. In embodiments which include a covering, such as a fabric, mesh, textured weave, felt, looped or porous structure, as described and illustrated in U.S. patent Ser. No. 10/441,531, incorporated herein by reference for all purposes, the proximal element lines 90 may be connected to the proximal elements 16 by attachment to the covering itself or by passage of the proximal element lines 90 through the covering and attaching to the proximal elements 16 in any manner described.

In addition, lock lines 92 are shown in FIG. 1 connected with a release harness 108 of the locking mechanism 106. The lock lines 92 are used to lock and unlock the locking mechanism 106 as will be described below. The proximal element lines 90 and lock lines 92 may be comprised of any suitable material, typically wire, nitinol wire, cable, suture or thread, to name a few. In addition, the proximal element lines 90 and/or lock lines 92 may include a coating, such as Parylene®. Parylene® is a vapor deposited pinhole free protective film which is conformal and biocompatible. It is inert and protects against moisture, chemicals, and electrical charge.

Figure 3:
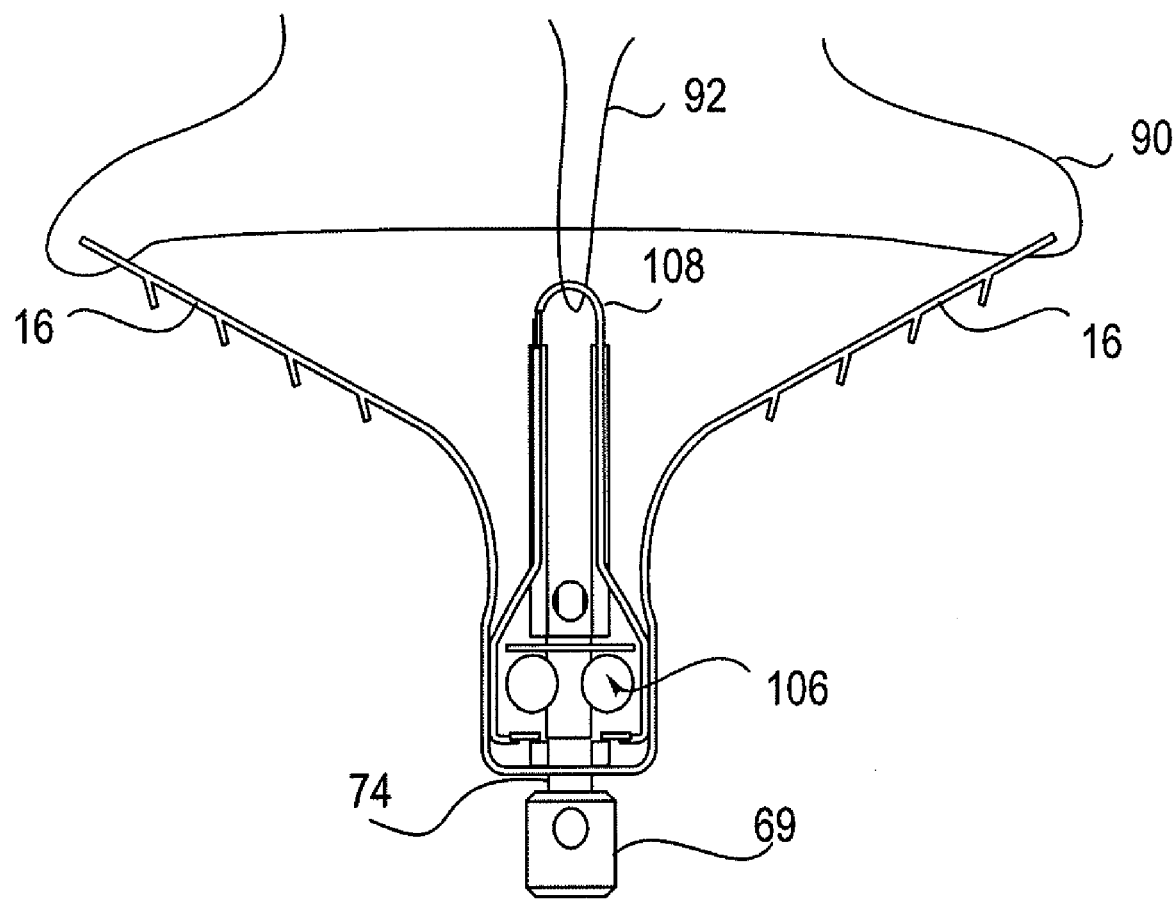
FIG. 3 provides a front view of the locking mechanism of FIG. 1.

FIG. 3 provides a front view of the locking mechanism 106 of FIG. 1. However, here the proximal elements 16 are supported by a single proximal element line 90 which is through both of the proximal elements 16. In this arrangement both of the elements are raised and lowered simultaneously by action of a single proximal element line 90. Whether the proximal elements 16 are manipulated individually by separate proximal element lines 90 or jointly by a single proximal element line 90, the proximal element lines 90 may extend directly through openings in the proximal elements and/or through a layer or portion of a covering on the proximal elements, or through a suture loop above or below a covering.

Figure 4A:
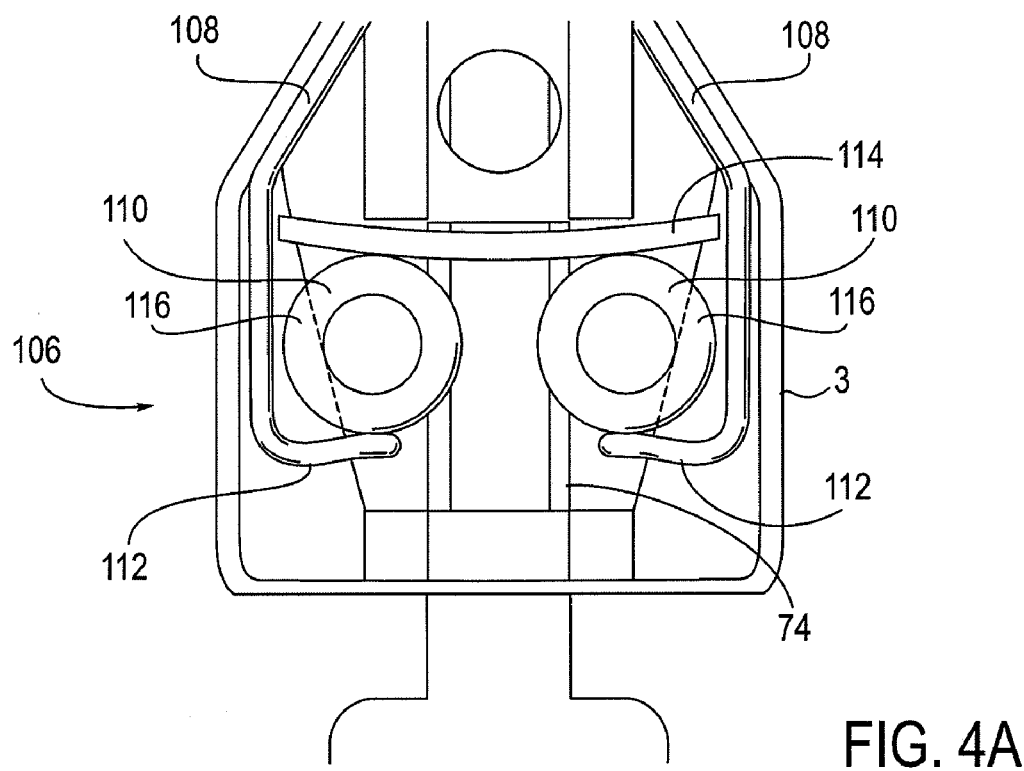
FIGS. 4A-4C illustrate the locking mechanism of FIG. 3 in unlocked and locked positions.
Figure 4B:
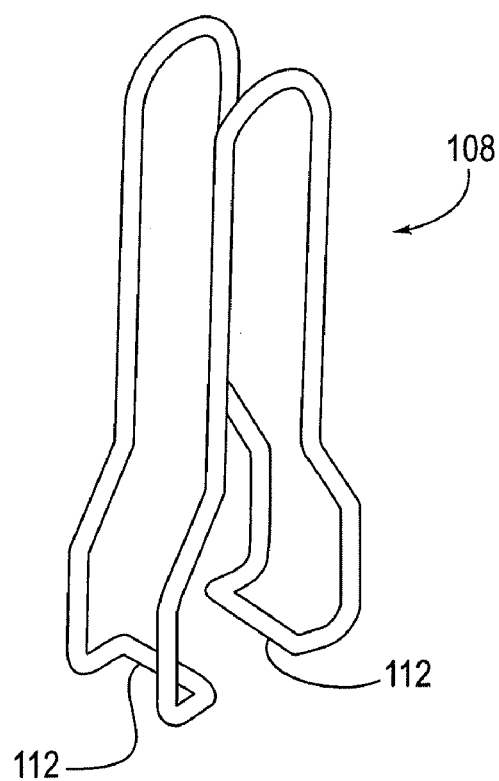
Figure 4C:
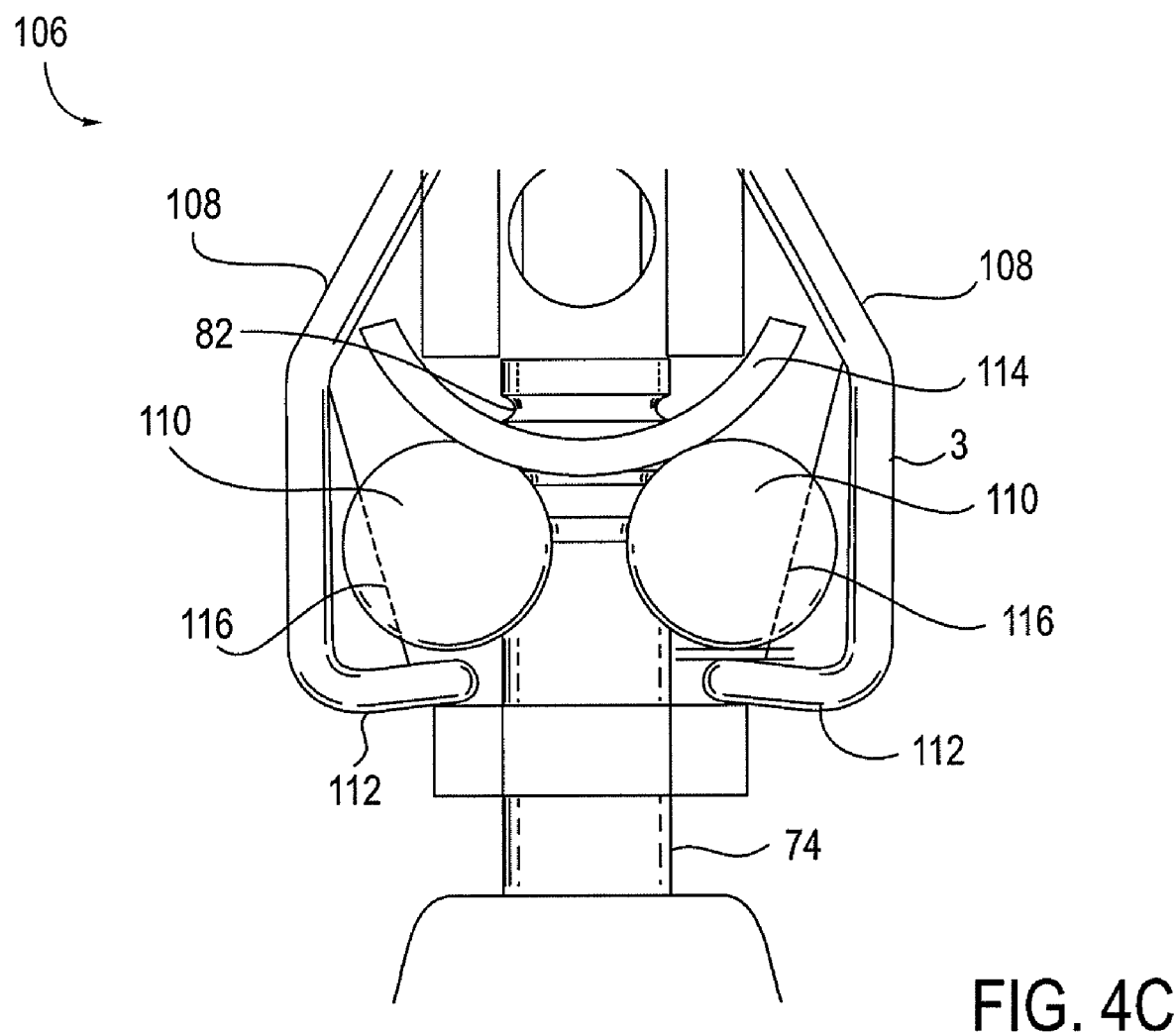

FIGS. 4A-4C illustrate the locking mechanism 106 showing the locking mechanism 106 in the unlocked and locked positions respectively. Referring to FIG. 4A, the locking mechanism 106 includes one or more engagement elements, such as wedging elements or rolling elements. In this embodiment, the wedging elements comprise a pair of barbells 110 disposed on opposite sides of the stud 74, each barbell having a pair of generally cylindrical caps and a shaft therebetween. The barbells 110 and the stud 74 are preferably comprised of cobalt chromium or stainless steel, however any suitable material may be used.

In some embodiments, each barbell 10 has a higher hardness than the stud 74. This hardness difference can enhance the grip or friction of the surfaces by allowing one element to "dig into" or invaginate into the other surface, even if only slightly. In addition, to improve engagement of the barbells 110 with the stud 74, the stud 74 may include one or more surface treatments and/or the stud 74 may have a particular composition and/or geometry, such as roughened surfaces, raised protrusions formed on the surface, frictional elements embedded in the surface, etc., to enhance surface friction and thereby increase the engagement strength.

The barbells 110 are manipulated by hooked ends 112 of the release harness 108. A perspective view of an embodiment of the release harness 108 is illustrated in FIG. 4B. When an upwards force is applied to the harness 108 by the lock line 92 (illustrated in FIG. 1), the hooked ends 112 raise the barbells 110 against a spring 114, as shown in FIG. 4A. This draws the barbells 110 up along a sidewall or sloping surface 116 which unwedges the barbells 110 from against the stud 74. In this position, the stud 74 is free to move. Thus, when the lock line 92 raises or lifts the harness 108, the locking mechanism 106 is in an unlocked position wherein the stud 74 is free to move the actuation mechanism 58 and therefore the distal elements 18 to any desired position. Release of the harness 108 by the lock line 92 transitions the locking mechanism 106 to a locked position, illustrated in FIG. 4C. By releasing the upwards force on the barbells 110 by the hooked ends 112, the spring 114 forces the barbells 110 downwards and wedges the barbells 110 between the sloping surface 116 and the stud 74. This restricts motion of the stud 74, which in turn locks the actuation mechanism 58 and therefore distal elements 18 in place.

In addition, the stud 74 may include one or more grooves 82 or indentations which receive the barbells 110. This may provide more rapid and positive locking by causing the barbells 110 to settle in a definite position, increase the stability of the locking feature by further preventing movement of the barbells 110, as well as tangible indication to the user that the barbell has reached a locking position. In addition, the grooves 82 may be used to indicate the relative position of the distal elements 18, particularly the distance between the distal elements 18. For example, each groove 82 may be positioned to correspond with a 0.5 or 1.0 mm decrease in distance between the distal elements 18. As the stud 74 is moved, the barbells 110 will contact the grooves 82; by counting the number of grooves 82 that are felt as the stud 74 is moved, the user can determine the distance between the distal elements 18 and can provide the desired degree of coaptation based upon leaflet thickness, geometry, spacing, blood flow dynamics and other factors. Thus, the grooves 82 may provide tactile feedback to the user, and may also be visible on fluoroscopy or an echocardiogram to provide visual feedback. Further, the grooves 82 may be sized to allow shifting or movement of each barbells 110 within each groove 82. Such shifting allows the stud 74 to move slightly in the proximal and distal direction, therefore allowing slight movement of the distal elements 18 when the locking mechanism is in the locked position. This may allow the fixation device 14 to open slightly in response to dynamic cardiac forces.

As mentioned, the locking mechanism 106 allows the fixation device 14 to remain in an unlocked position when attached to the interventional tool 10 during grasping and repositioning and then maintain a locked position when left behind as an implant. It may be appreciated, however, that the locking mechanism 106 may be repeatedly locked and unlocked throughout the placement of the fixation device 14 if desired. Further, the locking mechanism 106 depicted in FIGS. 1-3, 4A-4C allows the fixation device 14 to be incrementally moved toward the closed position while locked. As mentioned, movement toward the closed position is achieved by retracting or pulling the stud 74 in the proximal direction so that the distal elements 18 approach each other. Retraction of the stud 74 draws the barbells 110 upward. Since the sloping surfaces 116 widen in the proximal direction, the barbells 110 are allowed to unwedge in this direction. In contrast, extension or pushing of the stud 74 in the distal direction is resisted by further wedging of the barbells 110 between the sloping surfaces 116 and the stud. Once the final placement is determined, the lock line 92 and proximal element lines 90 are removed and the fixation device is left behind.

Figure 5:
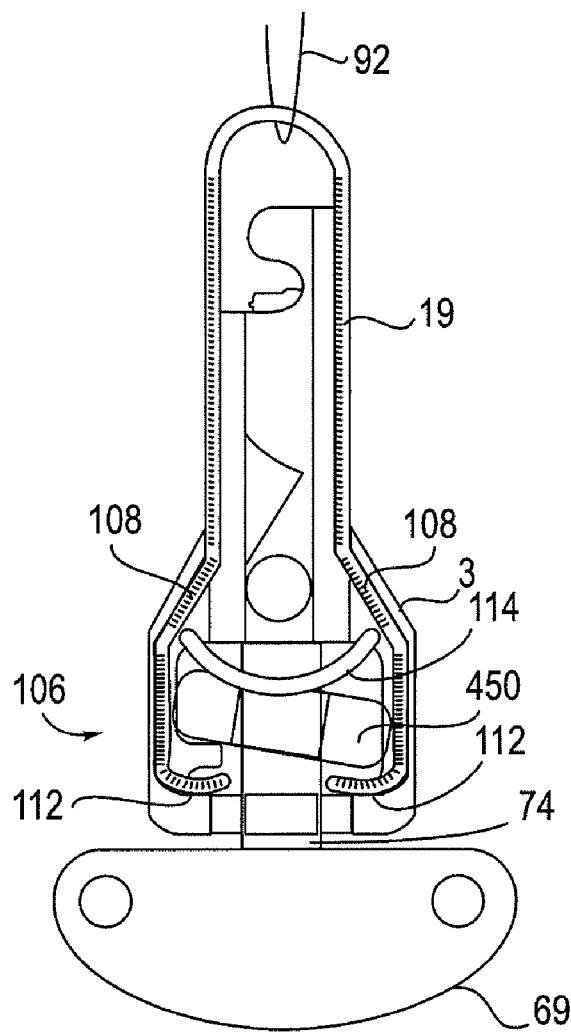
FIGS. 5-7 illustrate elements of an embodiment of a locking mechanism which includes a binding plate.
Figure 6:
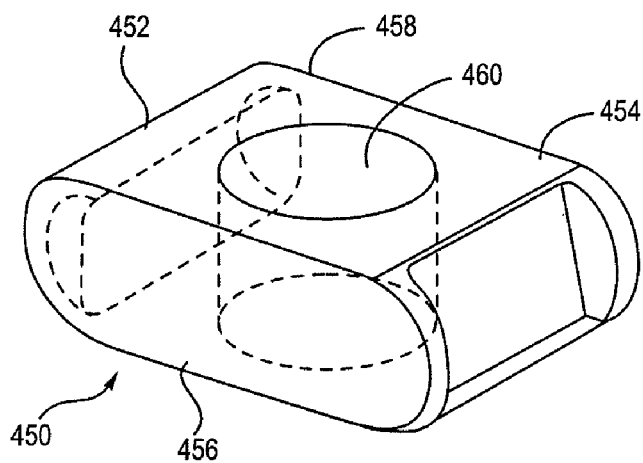
Figure 7:
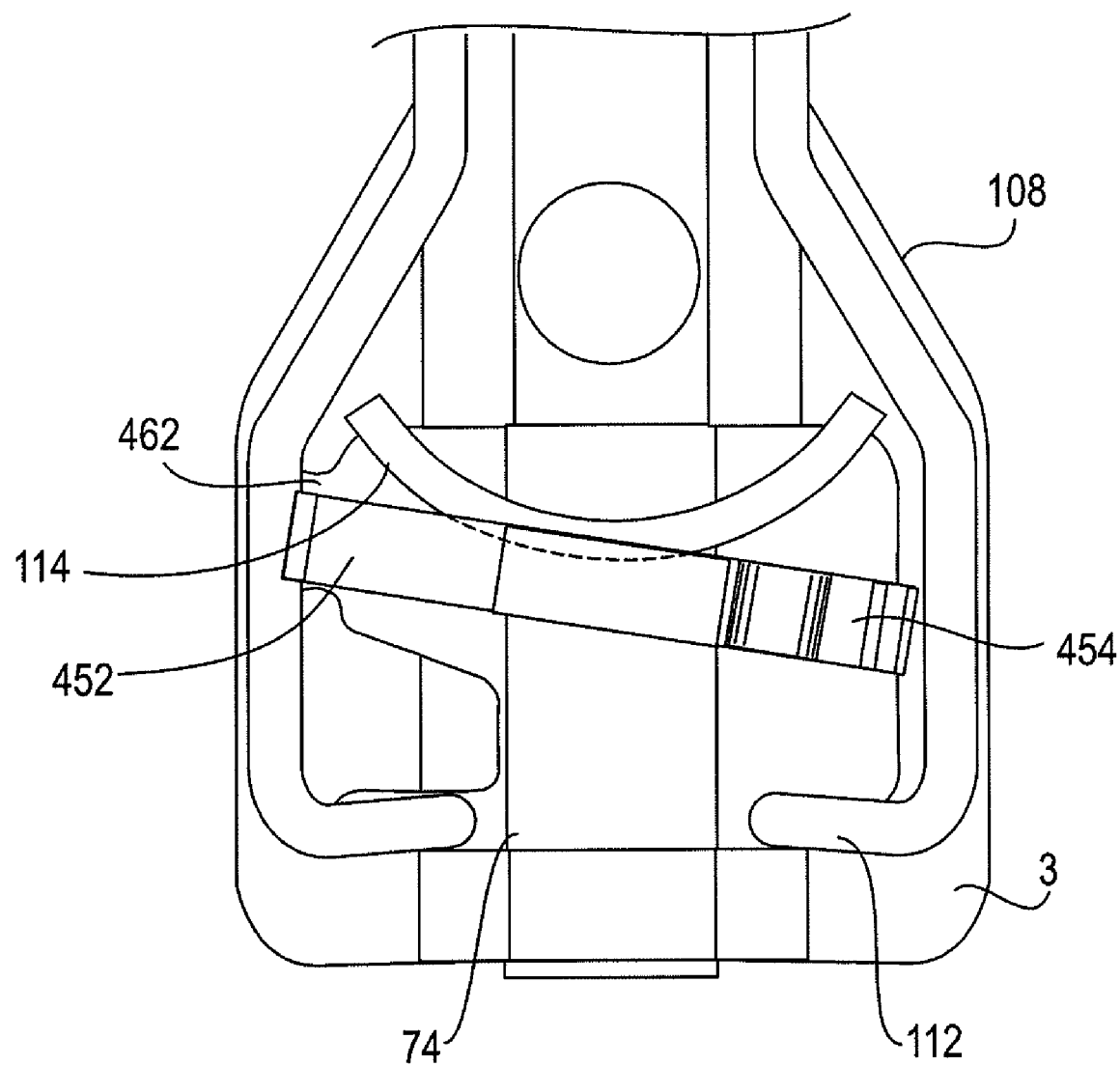

FIG. 5 illustrates another embodiment of a locking mechanism 106. In this embodiment, the locking mechanism 106 also includes an engagement element comprising a wedging element. Here the wedging element comprises a binding lever or binding plate 450. In this embodiment, as shown in FIG. 6, the binding plate 450 has an oblong shape extending between a first end 452 and a second end 454 with a bottom planar surface 456 and a top planar surface 458. An aperture 460 is formed between the first and second ends 452, 454 extending from the top planar surface 458 through to the bottom planar surface 456. Referring back to FIG. 5, the binding plate 450 is positioned within the locking mechanism 106 so that the stud 74 passes through the aperture 460. FIG. 7 provides a closer view of the binding plate 450 within the locking mechanism 106. As shown, the first end 452 is positioned within a notch 462 which prevents axial movement of the first end 452. However, the second end 454 is free to move in an axial direction thus creating a lever type movement of the binding plate 450. Movement of the second end 454 is controlled by the associated hooked end 112 of the release harness 108. When an upwards force is applied to the harness 108 by the lock line 92, the hooked end 112 raises the second end 454 of the plate 450 against a spring 114 so that the planar surfaces 456, 458 are substantially perpendicular to the stud 74. This aligns the aperture 460 with the stud 74 allowing free movement of the stud 74. Thus, in this state, the locking mechanism 106 is unlocked wherein the stud 74 is free to move the actuation mechanism 58 and therefore the distal elements 18 to any desired position.

Release of the harness 108 by the lock line 92 transitions the locking mechanism 106 to a locked position. By releasing the upwards force on the second end 452 of the binding plate 450, the spring 114 forces the second end 452 downwards and wedges the aperture 460 against the stud 74, as illustrated in FIG. 5 and FIG. 7. This restricts motion of the stud 74, which in turn locks the actuation mechanism 58 and therefore distal elements 18 in place. It may be appreciated that the binding plate 450 may have any suitable form to function as described above. For example, the plate 450 may have a variety of shapes with or without planar surfaces 456, 458 and/or the aperture 460 may be of a variety of shapes and positioned in a variety of locations, to name a few. Further, it may be appreciated that any number of binding plates 450 may be present. Each binding plate 450 provides an additional binding location which may enhance lock performance.

It may be appreciated that although the above described embodiment of the binding plate 450 includes an aperture 460 for passing of the stud 74 therethrough, the binding plate 450 may be shaped so as to not include such an aperture 460. In such embodiments, the binding plate 450 may be shaped to at least partially surround the stud 74, such as having a notch, inlet or hook-shape through which the stud 74 passes. Thus, the binding plate 450 would function in the same manner as above wherein the portion at least partially surrounding the stud 74 would engage the stud 74 for locking and disengage the stud 74 for unlocking.

The binding plate 450 and the stud 74 may be comprised any suitable material. In some embodiments, the binding plate 450 has a higher hardness than the stud 74. In other embodiments, the binding plate 450 is comprised of a flexible or semi-flexible material. Such flexibility allows slight movement of the stud 74 in the proximal and distal directions, therefore allowing slight movement of the distal elements 18 when the locking mechanism is in the locked position. This may allow the fixation device 14 to adjust in response to dynamic cardiac forces.

To improve engagement of the binding plate 450 with the stud 74, the stud 74 may include one or more surface treatments and/or the stud 74 may have a particular composition and/or geometry as set forth above.

In this embodiment the stud 74 may include one or more grooves 82 or indentations which receive the binding plate 450, similar to the grooves of the locking mechanism of FIGS. 1-3, 4A-4C. Again, this may provide more rapid and positive locking by causing the binding plate 450 to settle in a definite position, increase the stability of the locking feature by further preventing movement of the binding plate 450, as well as tangible indication to the user that the binding plate 450 has reached a locking position. In addition, the grooves 82 may be used to indicate the relative position of the distal elements 18, particularly the distance between the distal elements 18.

The locking mechanism 106 depicted in FIG. 5 allows the fixation device 14 to be incrementally moved toward the closed position while locked. Movement toward the closed position is achieved by retracting or pulling the stud 74 in the proximal direction so that the distal elements 18 approach each other. Retraction of the stud 74 draws the binding plate 450 towards a horizontal position, aligning the aperture with the stud 74 and thus allowing movement. In contrast, extension or pushing of the stud 74 in the distal direction is resisted by further wedging of the binding plate 450 against the stud 74. Once the final placement is determined, the lock line 92 and proximal element lines 90 are removed and the fixation device is left behind.

Figure 8B:
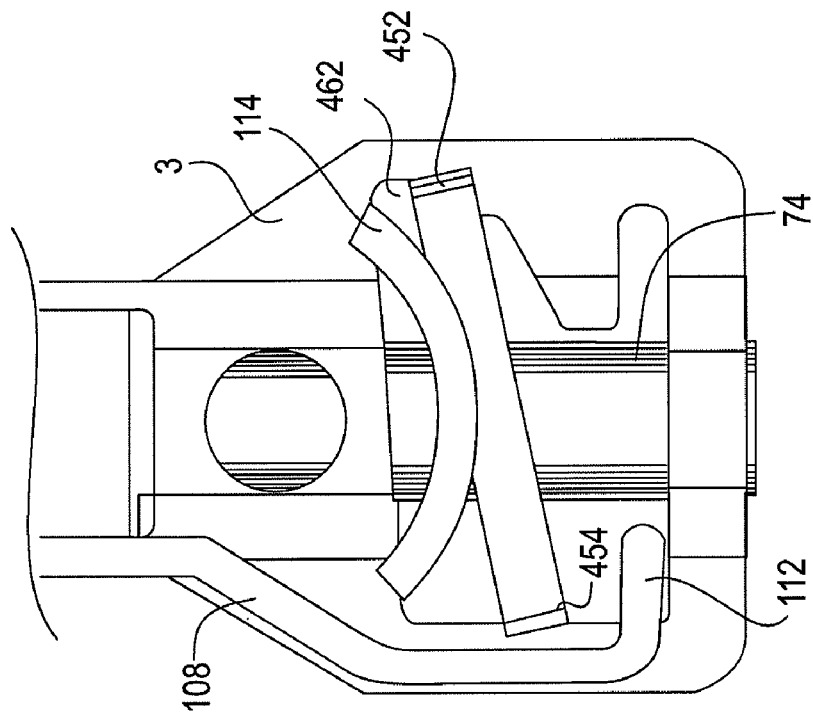
FIGS. 8A-8B illustrate an embodiment of a locking mechanism having a one-sided release harness.
Figure 8A:
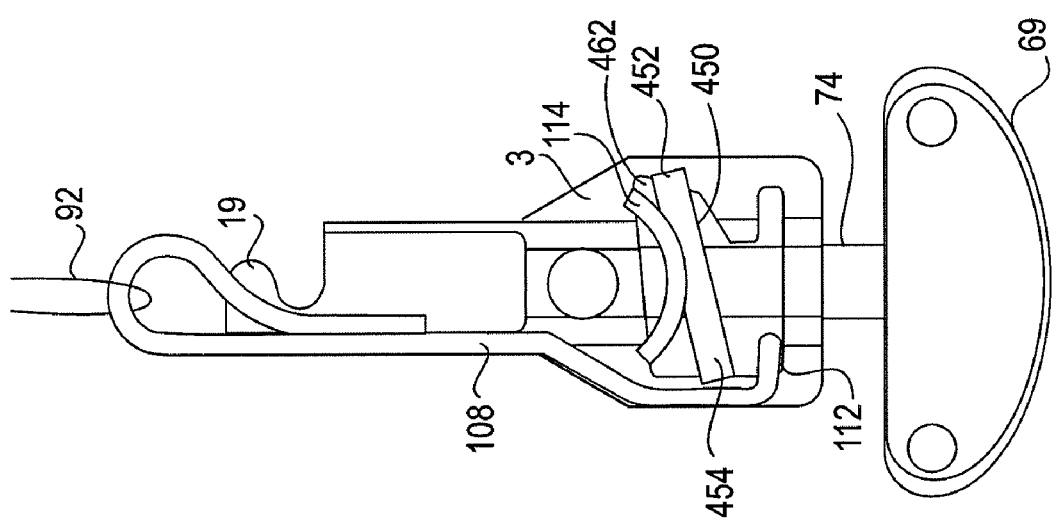

FIGS. 8A-8B illustrate a similar embodiment of a locking mechanism. Again, the wedging element comprises a binding plate 450 positioned within the housing 3 so that the stud 74 passes through the aperture 460. FIG. 8B provides a closer view of the binding plate 450 within the housing 3. As shown, the first end 452 of the lever 450 is positioned within a notch 462 which prevents axial movement of the first end 452. However, the second end 454 of the binding plate 450 is free to move in an axial direction thus creating a lever type movement of the binding plate 450. Movement of the second end 454 is controlled by the associated hooked end 112 of the release harness 108. Here, the release harness 108 is "one-sided" in comparison to the release harness of FIG. 5, i.e. only one hooked end 112 is present. When an upwards force is applied to the harness 108 by the lock line 92, the hooked end 112 raises the second end 454 of the plate 450 against a spring 114 so that plate 450 is substantially perpendicular to the stud 74. This aligns the aperture 460 with the stud 74 allowing free movement of the stud 74. Thus, in this state, the locking mechanism 106 is unlocked wherein the stud 74 is free to move the actuation mechanism 58 and therefore the distal elements 18 to any desired position. The "one-sided" harness improves ease of use and unlocking consistency throughout various fixation device positions.

Release of the harness 108 by the lock line 92 transitions the locking mechanism 106 to a locked position. By releasing the upwards force on the second end 452 of the binding plate 450, the spring 114 forces the second end 452 downwards and wedges the aperture 460 against the stud 74. This restricts motion of the stud 74, which in turn locks the actuation mechanism 58 and therefore distal elements 18 in place.

Figure 9A:
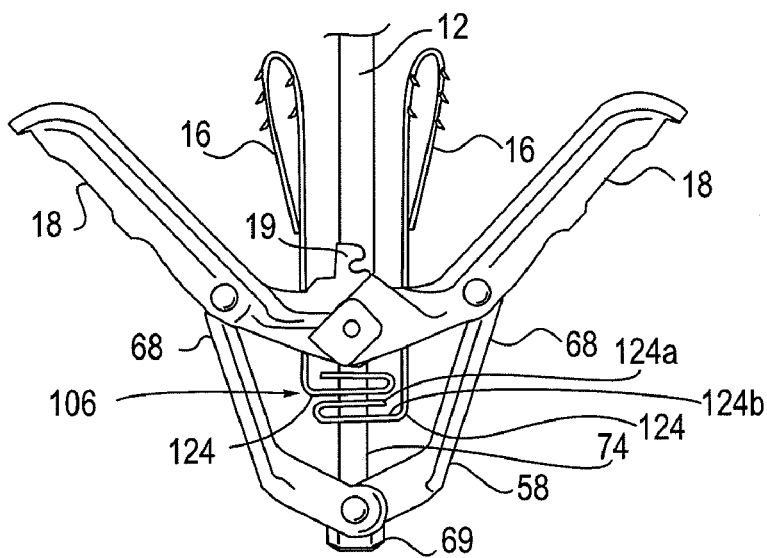
FIGS. 9A-9C illustrate an embodiment of a locking mechanism having wedging elements comprising binding structures.
Figure 9B:
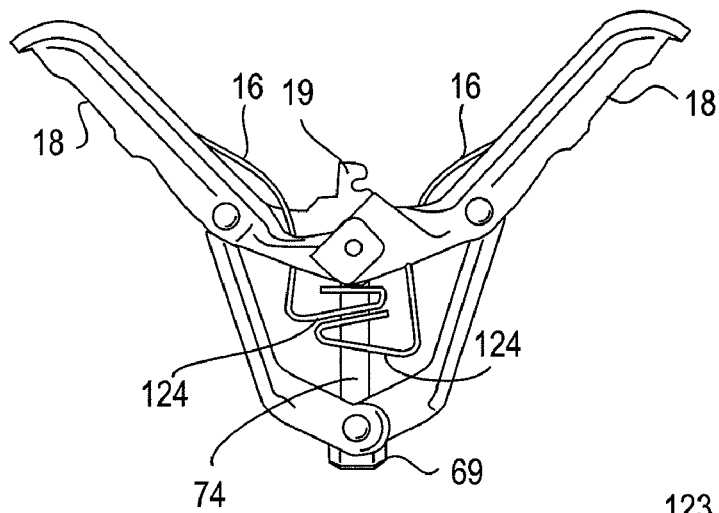
Figure 9C:
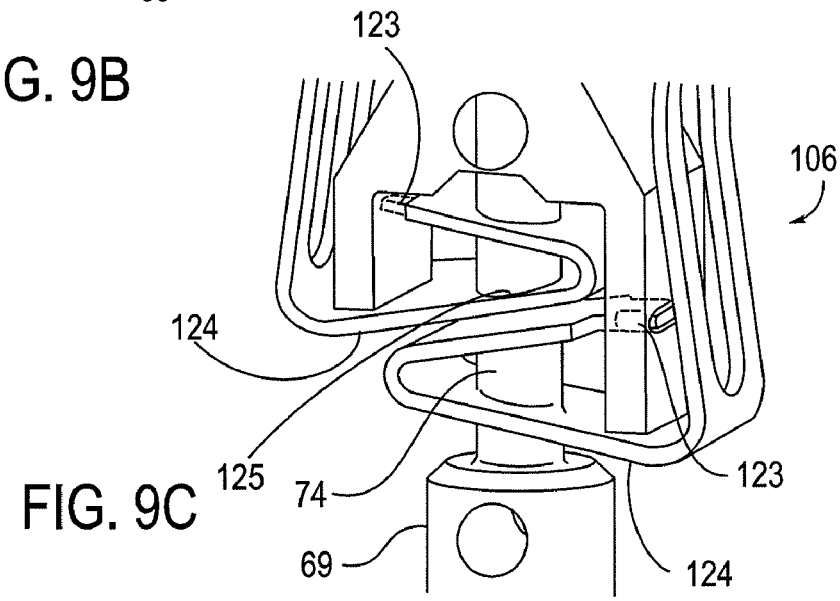

FIGS. 9A-9C illustrate another embodiment of a locking mechanism 106. Referring to FIG. 9A, in this embodiment, the locking mechanism 106 is again disposed between the coupling member 19 and the base 69 of the actuation mechanism 58. The base 69 is connected to the stud 74 which extends through the locking mechanism 106, and connects to an actuator rod which extends through the coupling member 19 and the shaft 12 of the interventional tool 10. The base 69 is also connected to the legs 68 of the actuation mechanism 58 which are in turn connected to the distal elements 18. FIG. 9A also illustrates proximal elements 16 which manipulate the locking mechanism 106 in this embodiment. The locking mechanism 106 includes wedging elements comprising folded leaf or binding structures 124 having overlapping portions 124a, 124b. Each folded binding structure 124 is attached to or continuously formed with a proximal element 16, as shown. In FIG. 9A and FIG. 9B, the folded structures 124 are shown without the remainder of the locking mechanism 106 (housing) for clarity. The proximal elements 16 are flexible, resilient and biased outwardly. The binding structures 124 include holes 125 (FIG. 9C) in each overlapping portion 124a, 124b so that the stud 74 passes through the holes 125 of the portions 124a, 124b as shown. The locking mechanism includes slots into which ends 123 of the binding structures 124 are fixed. When the proximal elements 16 are in an undeployed position, as in FIG. 9A, the binding structures 124 lie substantially perpendicular to the stud 74 so that the holes 125 in each overlapping portion are vertically aligned. This allows the stud 74 to pass freely through the holes and the locking mechanism 106 is considered to be in an unlocked position.

Deployment of the proximal elements 16, as shown in FIG. 9B, tilts the binding structures 124 so as to be disposed in a non-perpendicular orientation relative to the stud 74 and the holes 125 are no longer vertically aligned with one another. In this arrangement, the stud 74 is not free to move due to friction against the holes of the binding structure 124. FIG. 9C provides a larger perspective view of the folded structures 124 in this position. Thus, the locking mechanism 106 is considered to be in a locked position. This arrangement allows the fixation device 14 to maintain an unlocked position during grasping and repositioning and then maintain a locked position when the proximal elements 16 are deployed and the fixation device 14 is left behind as an implant. This arrangement also allows locking to be achieved automatically by releasing of the proximal elements 16. Therefore, there is no need for a separate actuator for the locking mechanism. Such as combined function of grasping and locking, thereby eliminating the need for separate actuation elements, may reduce the profile and complexity of the fixation device, simplifying the user interface. It may also be appreciated, that the locking mechanism 106 may be repeatedly locked and unlocked throughout the placement of the fixation device 14 if desired.

Figure 10A:
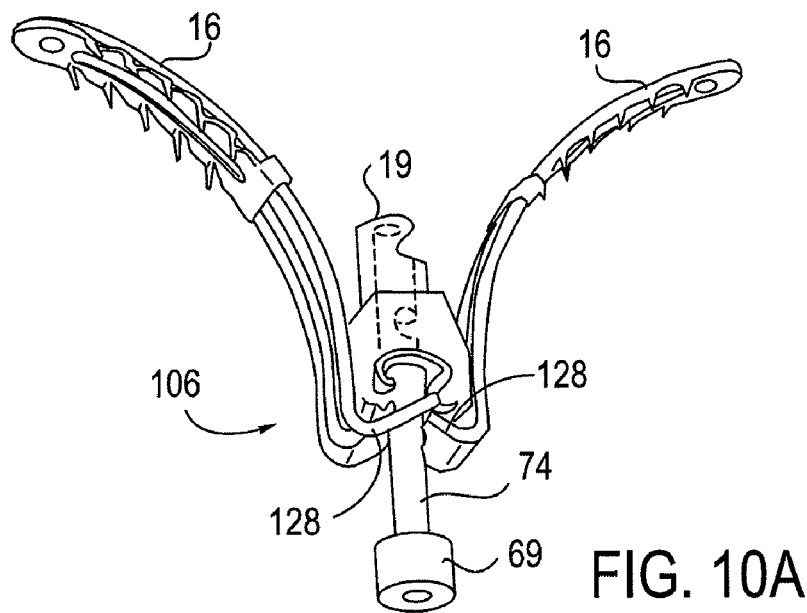
FIGS. 10A-10C illustrate an embodiment of a locking mechanism having wedging elements comprising interdigitating structures.
Figure 10B:
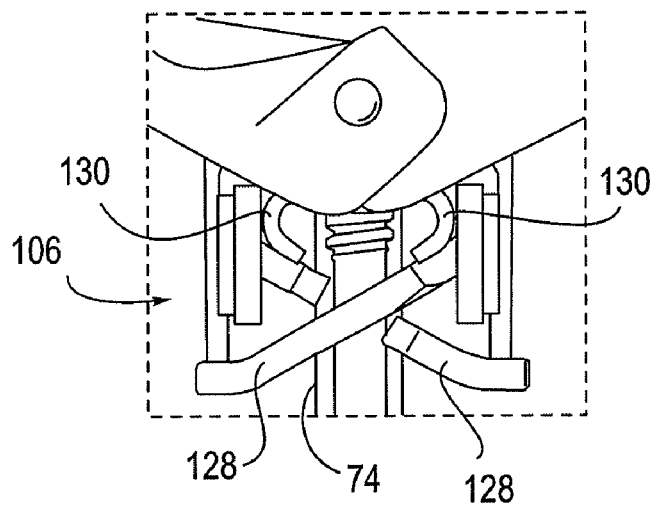
Figure 10C:
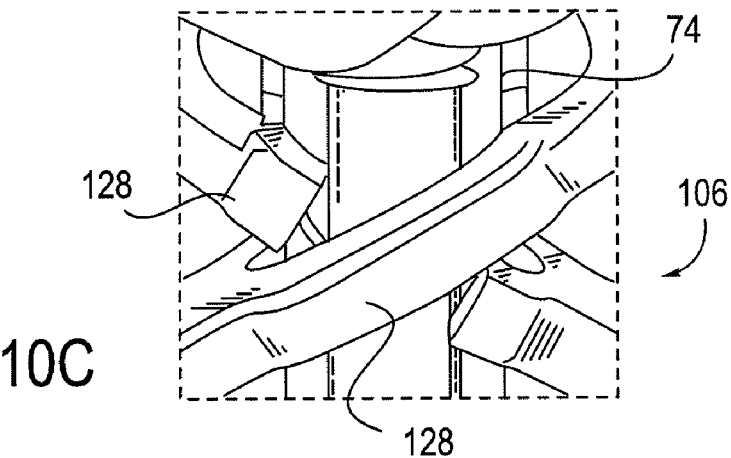

FIGS. 10A-10C illustrate a similar embodiment of a locking mechanism 106. Referring to FIG. 10A, in this embodiment, the locking mechanism 106 is again disposed between the coupling member 19 and the base 69 of the actuation mechanism 58. And, the base 69 is connected to the stud 74 which extends through the locking mechanism 106 and connects to an actuator rod which extends through the coupling member 19 and the shaft of the interventional tool 10. FIG. 10A illustrates the proximal elements 16 which manipulate the locking mechanism 106 in this embodiment. The locking mechanism 106 includes wedging elements comprising interdigitating structures 128, such as in the shape of a "C" as illustrated, each interdigitating structure 128 attached to a proximal element 16. The interdigitating structures 128 hook around the stud 74 so that the stud 74 passes through the "C" of each structure 128 as shown in FIGS. 10B-10C. As shown, the structures 128 cross each other and the "C" of each structure 128 faces each other. A spring 130 biases the interdigitating structures into engagement with one another. When the proximal elements are in an undeployed position, as in FIG. 10B, the interdigitating structures 128 are urged into an orientation more orthogonal to the axial direction defined by stud 74, thus bringing the "C" of each structure 128 into closer axial alignment. This allows the stud 74 to pass freely through the "C" of each structure 128. Deployment of the proximal elements 16 outwardly urges the interdigitating structures into a more angular, non-orthogonal orientation relative to stud 74 causing the sidewalls of the "C" of each structure 128 to engage stud 74 more forcefully. In this arrangement, the stud 74 is not free to move due to friction against the interdigitating structures 128.

Figure 11A:
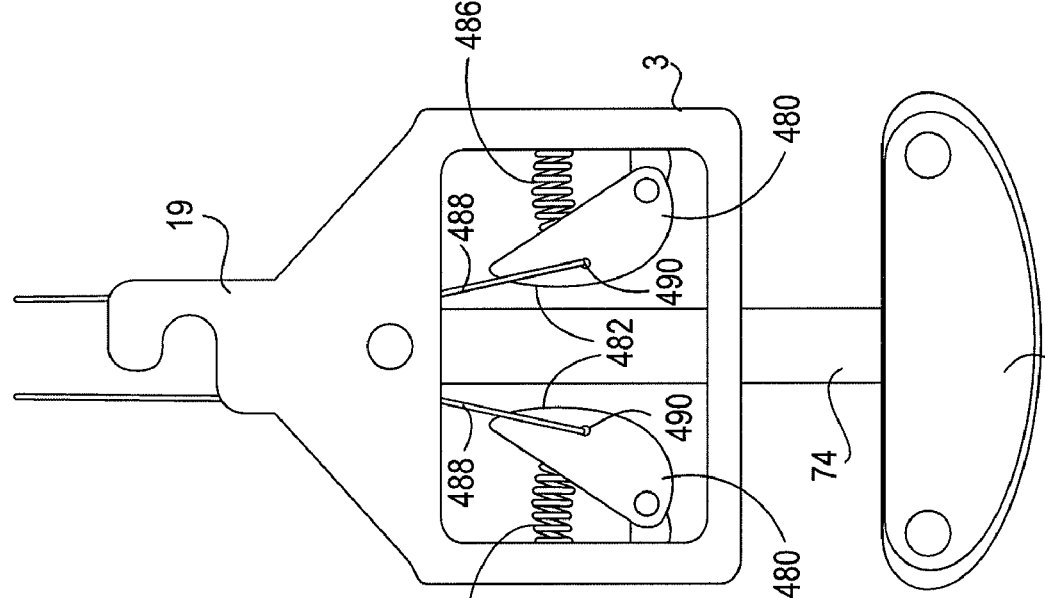
FIGS. 11A-11B illustrate an embodiment of a locking mechanism comprising a pair of cams.
Figure 11B:
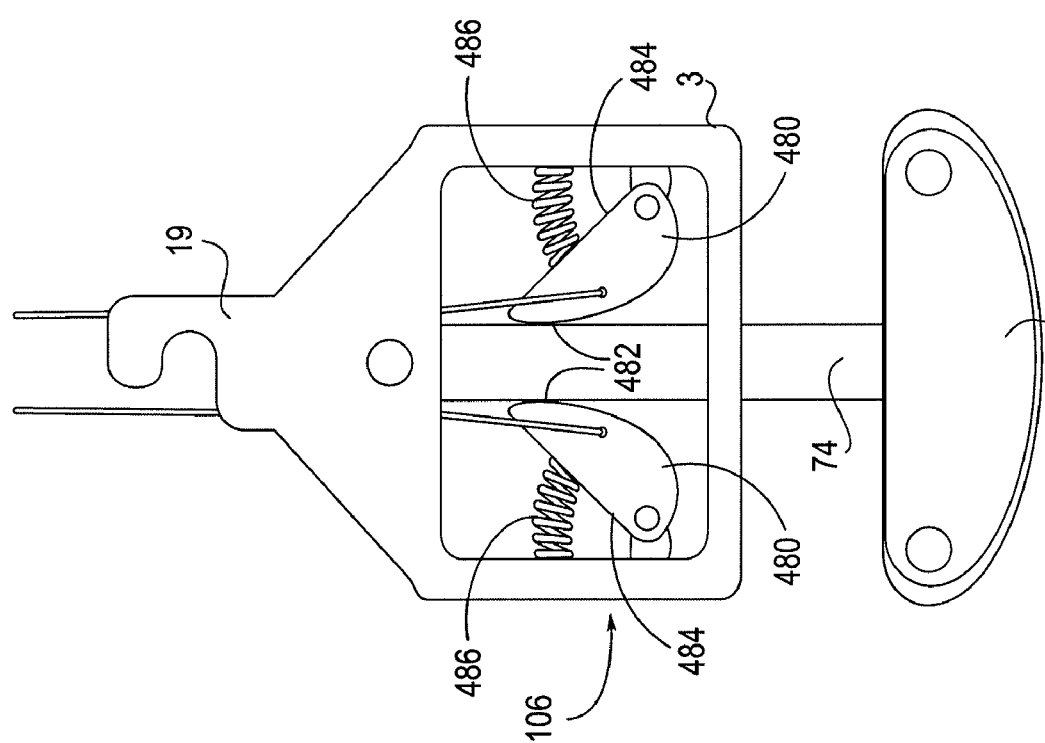

FIGS. 11A-11B illustrate another embodiment of a locking mechanism 106. In this embodiment, the locking mechanism 106 also includes at least one wedging element. Here each wedging element comprises a cam 480. FIG. 11A illustrates a pair of cams 480 disposed on opposite sides of the stud 74, each cam 480 having an inward surface 482 and an outward surface 484. Each cam 480 is connected to a wall of the locking mechanism 106 by a spring 486 or other mechanism which applies force to the outward surface 484 of the cam 480. Such force wedges the inward surface 482 of the cam 480 against the stud 74, as shown in FIG. 11A, when in the locked position. Thus, when the cams 480 are wedged against the stud 74 the stud 74 is not free to move and therefore the distal elements 18 are locked in place.

Each cam 480 is coupled with a actuator 488 at a pivot point 490. By applying an upwards force on actuator 488, the associated cam is pivoted around pivot point 490 so that its inward surface 482 is unwedged from the stud 74, as illustrated in FIG. 11B. In this position, the stud 74 is free to move. Thus, when the cams 480 are pivoted the locking mechanism 106 is in an unlocked position wherein the stud 74 is free to move the actuation mechanism 58 and therefore the distal elements 18 to any desired position. It may be appreciated that any number of cams 480 may be present and each cam 480 may have any suitable form to function as described above.

Figure 12A:
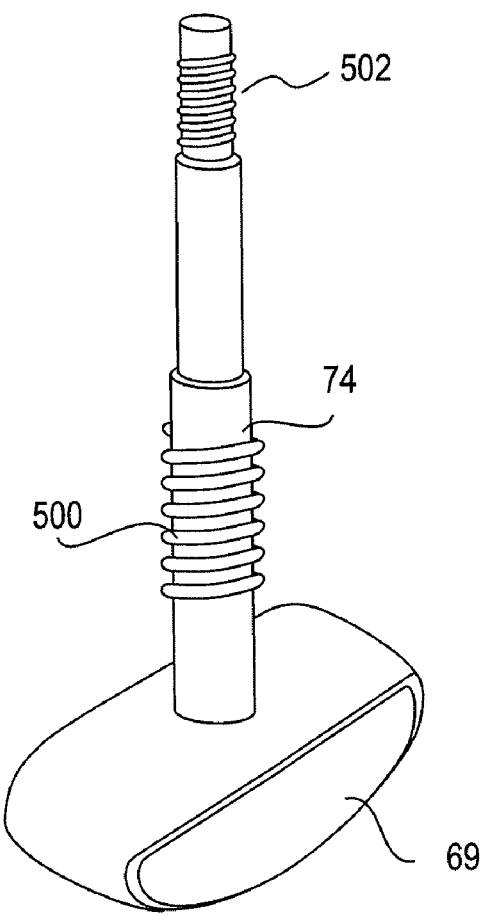
FIGS. 12A-12D illustrate elements of an embodiment of a locking mechanism which includes mateable components having at least one protrusion and groove which engage for locking.
Figure 12B:
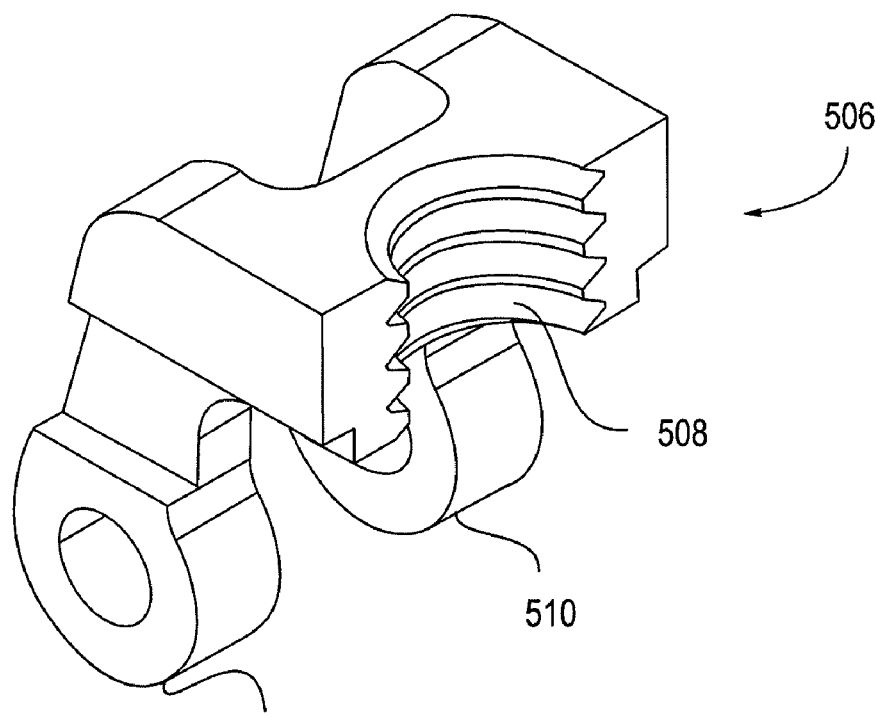

FIGS. 12A-12D illustrate another embodiment of a locking mechanism 106 having at least one engagement element. In this embodiment, the at least one engagement element has at least one protrusion which engages at least one groove on the stud 74 to lock the stud 74 in place. FIG. 12A illustrates an embodiment of a stud 74 of the present invention having external grooves along its surface, in this instance external threads 500. Here, the stud 74 is shown attached at one end to base 69 and having a threaded free end 502 which is coupleable with shaft 12 of the tool 10. It may be appreciated that the external grooves or threads 500 may extend along any distance of the surface of the stud 74 and may have any depth or spacing. Also it may be appreciated that the external grooves may comprise a series of cuts, indentations or threading which may or may not extend around the circumference of the stud 74. FIG. 12B illustrates an embodiment of the at least one engagement element having grooves, in this instance a split nut 506. The split nut 506 has a curved threaded surface 508 sized to mate with the external threads 500 of the stud 74. Each split nut 506 also has at least one hinge component 510 which is used to rotate or translate each split nut 506 within the locking mechanism 106 to engage or disengage the external threads 500 of the stud 74.

Figure 12C:
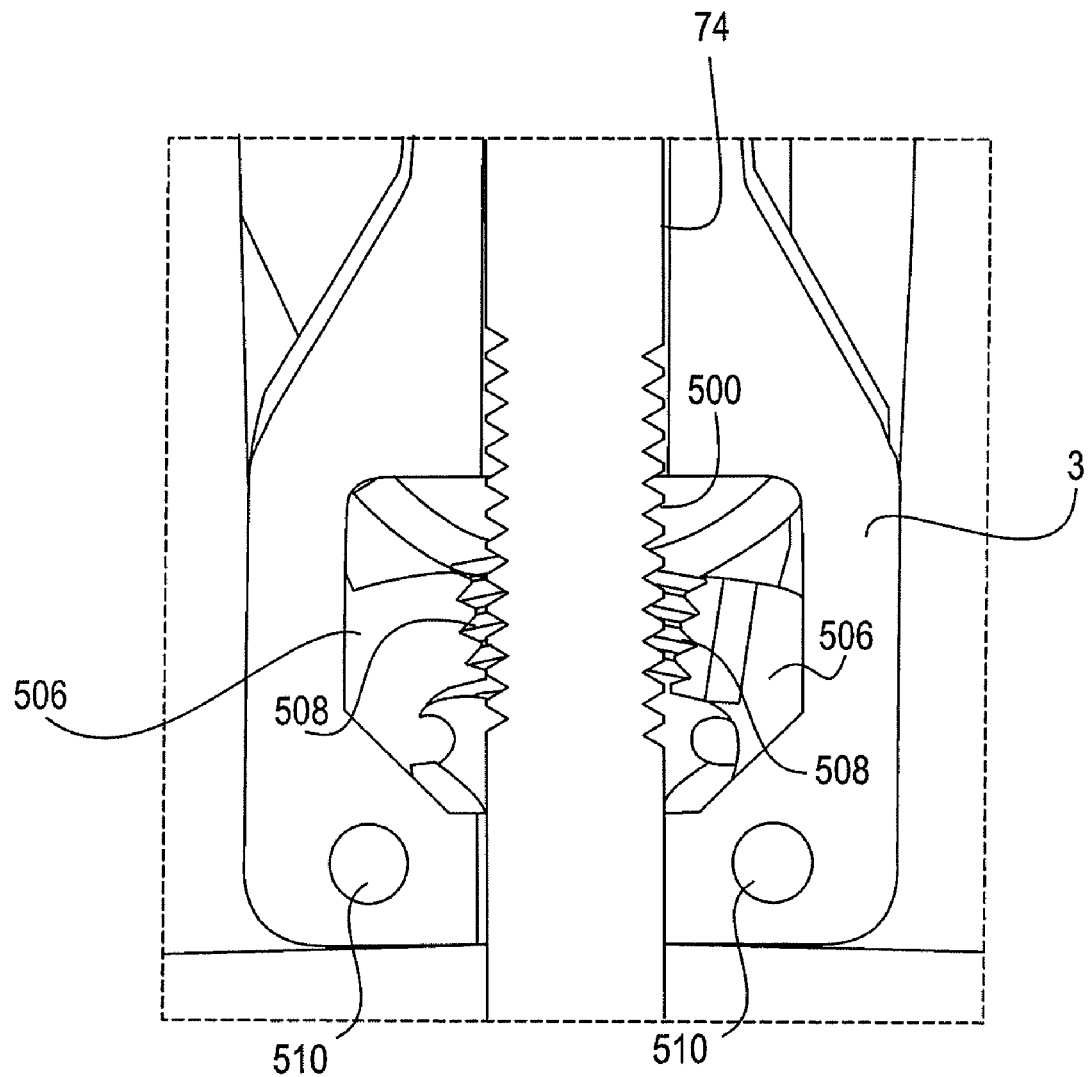

FIG. 12C illustrates a pair of split nuts 506 disposed on opposite sides of the stud 74, each split nut 506 having its curved threaded surface 508 facing the external threads 500 of the stud 74. The split nuts 506 are rotated or translated so that the threaded surfaces 508 are not engaging the external threads 500. In this position, the stud 74 is free to move. Thus, when the split nuts 506 are rotated or translated outward the locking mechanism 106 is in an unlocked position wherein the stud 74 is free to move the actuation mechanism 58 and therefore the distal elements 18 to any desired position. Rotation or translation of the split nuts 506 inward engages the curved threaded surfaces 508 with the external threads 500. Such engagement prevents motion of the stud 74, locking the distal elements 18 in place. It may be appreciated that any number of components may be present and each component may have any suitable form to function as described above.

Figure 12D:
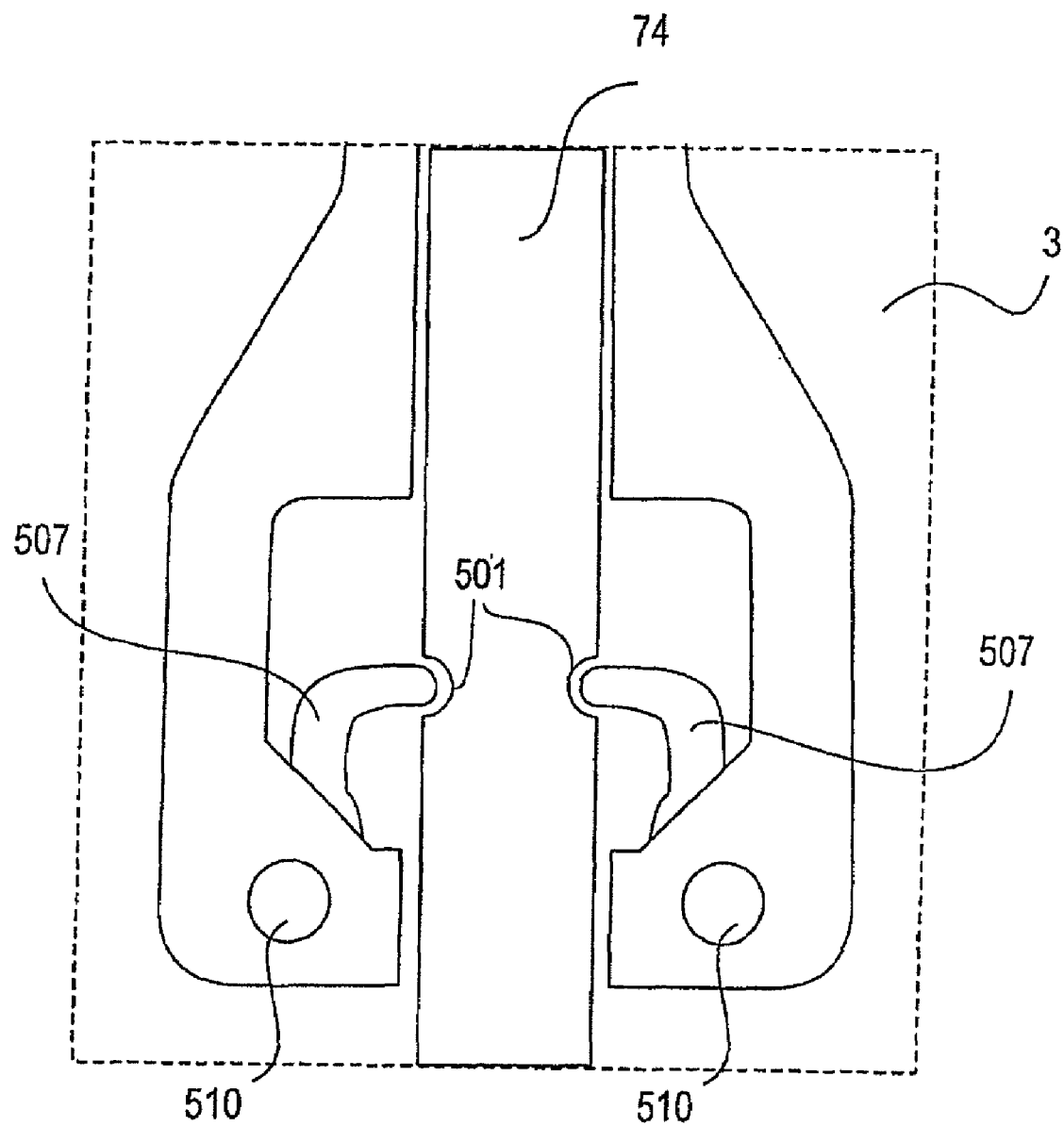

Many of the locking mechanisms of the present invention may be adapted for locking the fixation device 14 in a single predetermined position. Thus, rather than closing the distal elements 18 and locking the distal elements 18 in place at one of a multitude of optional locations, the distal elements 18 may be closed and locked at a single predetermined position, such as at a 15, 30, 45 or 60 degree angle. For example, as mentioned above, the stud 74 may include a single groove 82 or indentation which receives the barbells 110. This may provide more rapid locking by causing the barbells 110 to settle in a single position, as well as indicating to the user that the fixation device 14 is locked in a known configuration. Likewise, FIG. 12D illustrates a locking embodiment similar to the embodiment of FIG. 12C. Here, a split ring 507, rather than a split nut, is disposed on opposite sides of the stud 74. The split ring 507 has a curved projection 509 sized to mate with a groove 501 on the stud 74. Each split ring 507 also has at least one hinge component 510 which is used to rotate or translate each split ring 507 within the locking mechanism 106 to engage or disengage the groove 501 of the stud 74. For example, the split rings 507 may be rotated or translated so that the projections 509 are not engaging the groove 501. In this position, the stud 74 is free to move. Thus, when the split rings 507 are rotated or translated outward the locking mechanism 106 is in an unlocked position wherein the stud 74 is free to move the actuation mechanism 58 and therefore the distal elements 18. Rotation or translation of the split rings 507 inward engages the curved projections 507 with the groove 501. Such engagement prevents motion of the stud 74, locking the distal elements 18 in the predetermined position. It may be appreciated that any number of components may be present and each component may have any suitable form to function as described above.

Figure 13C:
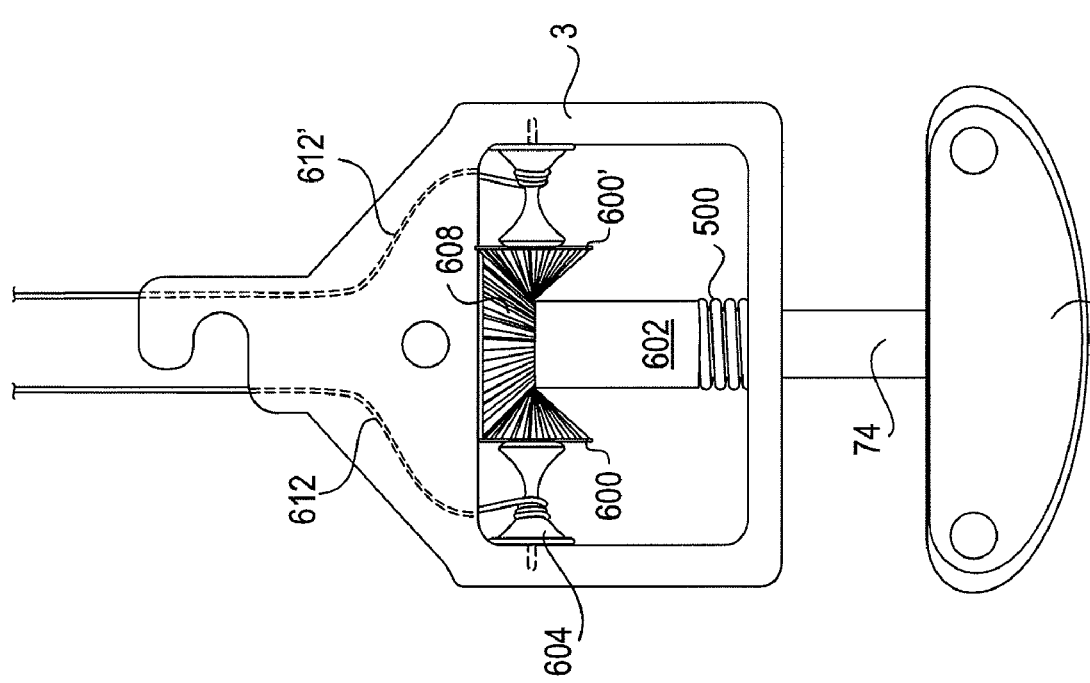
FIGS. 13A-13C illustrate an embodiment of a locking mechanism comprising gears.
Figure 13A:
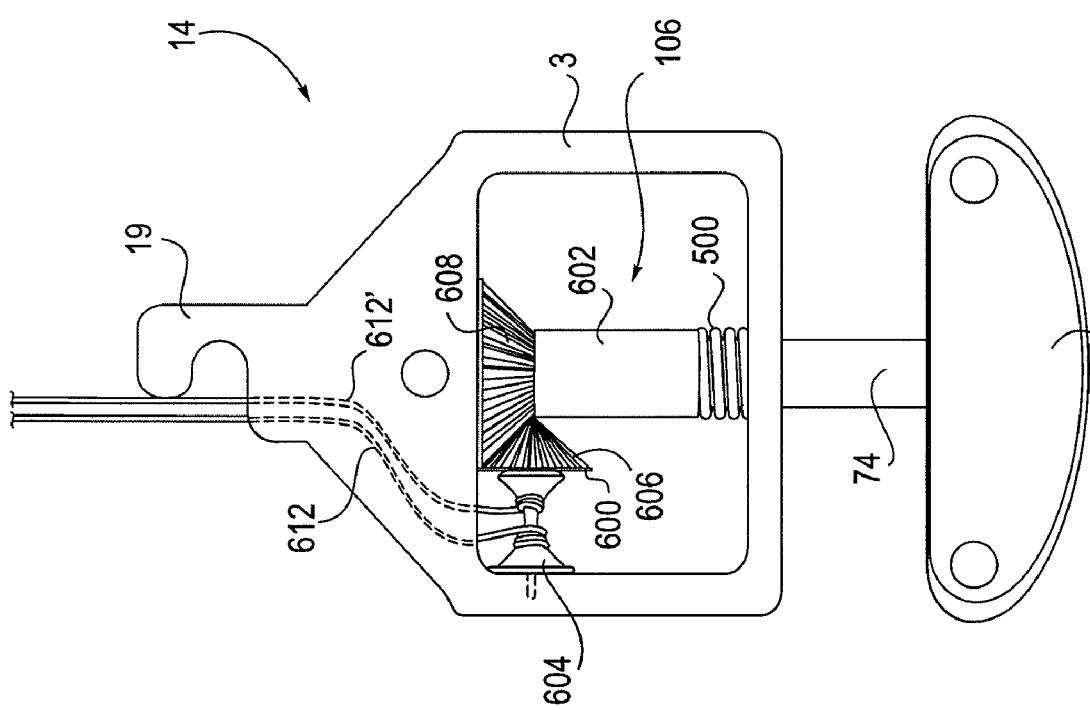
Figure 13B:
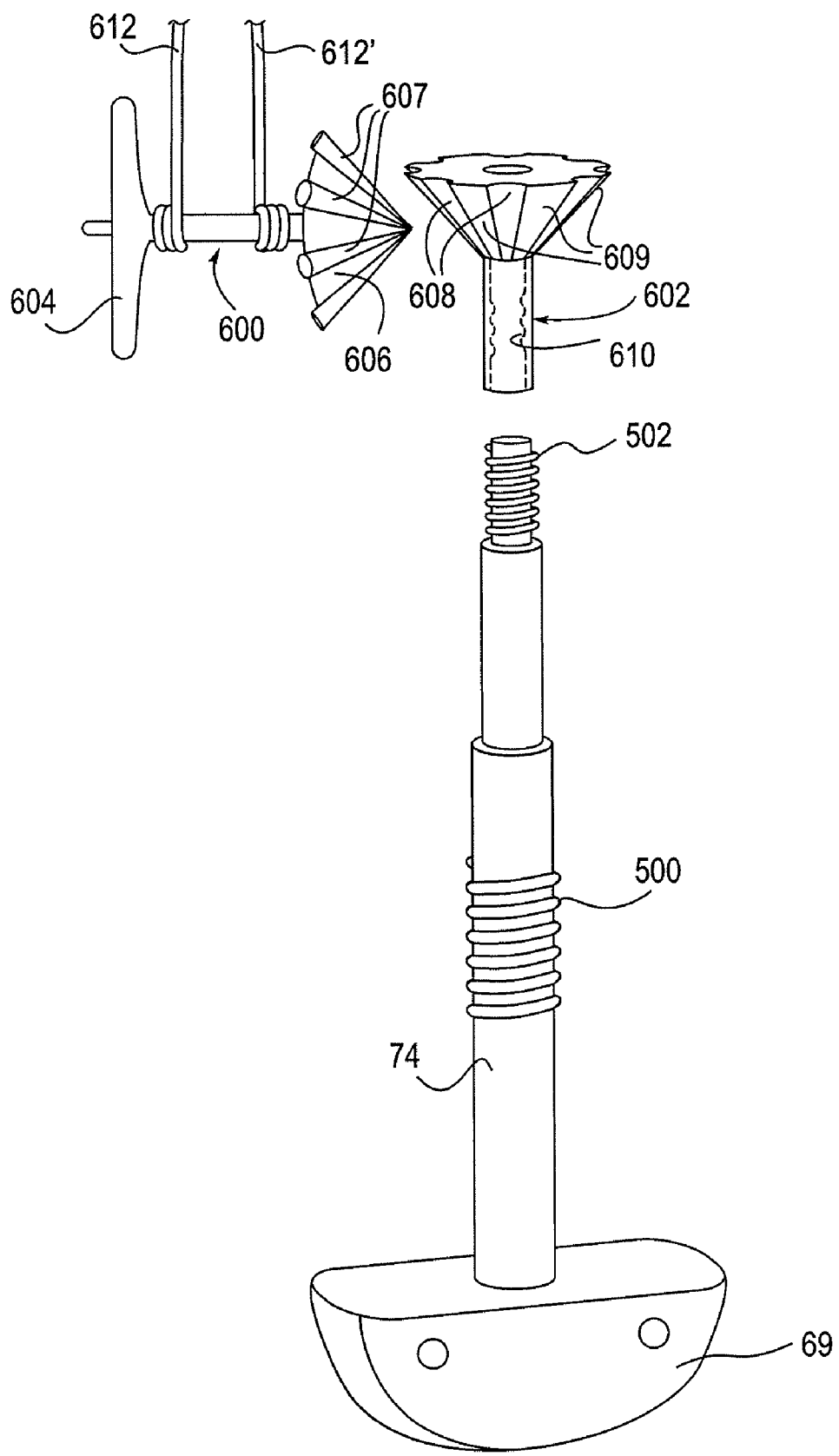

In some embodiments, the locking mechanism comprises gears. Such gears are used to incrementally translate the stud 74 in a forward or reverse direction which opens and closes the distal elements 18. Since translation of the stud 74 is controlled by the gears, the stud 74 is locked in place when the gears are not moving. Thus, no additional locking mechanism may be desired. FIGS. 13A-13C illustrate an embodiment of a fixation device 14 of the present invention having gears. Here, the stud 74 extends through the locking mechanism 106 as in previous embodiments. Advancement and retraction of the stud 74 moves the distal elements 18 (not show, for clarity) which are attached to the base 69. In this embodiment, the locking mechanism 106 comprises bevel gears. Referring to FIG. 13B, the bevel gears include a driving component 600 and a driven component 602. The driving component 600 has a pedestal 604 connectable with the housing 3 and a meshing surface 606 having gear teeth 607. The meshing surface 606 of the driving component 600 meshes with gear teeth 609 of a meshing surface 608 of the driven component 602 at an approximate angle of 90 degrees, or other suitable angle. The driven component 602 has a threaded interior 610 which mates with external threads 500 on the stud 74. Thus, rotation of the driven component 602 causes advancement or retraction of the stud 74. The driving component 600 may be rotated by any suitable mechanism, including a gear belt or gear line 612. In this embodiment, two gear lines 612, 612' are attached to the base 604 of the driving component 600. Each gear line 612, 612' is wound in the opposite direction so that pulling one gear line 612 rotates the driving component 600 in a clockwise direction and pulling the other gear line 612' rotates the driving component 600 in a counterclockwise direction. Alternatively, one gear line may be employed and operated in a clockwise or counterclockwise direction. The gear lines 612, 612' extend from the locking mechanism 106 through the coupling mechanism 19, as shown in FIG. 13A, and through the delivery catheter so as to be manipulable by the user outside of the body. In other embodiments, illustrated in FIG. 13C, two driving components 600, 600' may be present, each driving component 600, 600' meshed with the driven component 602. One gear line 612 is connected with one driving component 600 and the other gear line 612' is connected with the other driving component 600'. Pulling the gear line 612 rotates driving component 600 which rotates the driven component 602 causing advancement of the stud 74. Pulling the other gear line 612' rotates the other driving component 600' which rotates the driven component 602 in the opposite direction causing retraction of the stud 74. It may be appreciated that a variety of gear mechanisms may be used including spur gears, helical and herringbone gears, miter gears, worms and worm gears, hypoid gears and rack and pinions, to name a few.

In some embodiments, the locking mechanism works against biasing forces, either inherent in the fixation device or created by the grasped tissue. As mentioned, the fixation device 14 includes a stud 74 for moving the distal elements between open, closed, and inverted positions. In a "pull to close/push to open" embodiment, the distal elements 18 are pivotably coupled to the stud 74 by a pair of legs or link members, whereby pushing the stud 74 pivots the distal elements 18 inwardly toward the closed position. Once tissue has been grasped in a desired configuration (such as leaflets in a desired coapted arrangement), it may be desired to hold the stud 74 in place by a locking mechanism. In this embodiment, the grasped tissue biases the fixation toward the open position since it requires force to hold the tissues in place. Thus, the stud 74 is biased toward advancing ("pushing" to open). FIG. 14A illustrates the stud 74 extending through housing 3 and holding the distal elements in a desired position wherein the fixation device 14 is biased towards opening, i.e. the stud 74 is biased towards advancing. To lock or hold the stud 74 in place, an interference element, such as a locking sheath 640, is advanced over the stud 74, as illustrated in FIG. 14B. The locking sheath 640 fits snuggly over the stud 74 to prevent movement of the stud 74 relative to the sheath 640 by, for example, friction or by interlocking an internal threaded surface with threads 500 on the stud 74. The sheath 640 is advanced so that its distal end 642 abuts the housing 3 which is a stationary surface of the fixation device, as shown. Since the stud 74 is biased towards advancing, the distal end 642 of the sheath 640 is held against the housing 3 preventing advancement of the stud 74 and hence locking the stud 74 in place. Upon decoupling of the fixation device 14 for implantation, as illustrated in FIG. 14C, the distal end 642 of the sheath 640 may also be decoupled from its proximal end 644 for leaving behind with the fixation device 14. The distal end 642 may be removably joined with the proximal end 644 by any suitable mechanism. In one embodiment, illustrated in FIG. 14D, the proximal and distal ends 642, 644 each have projections 646 which are press-fit together in an alternating fashion. Thus, the proximal and distal ends 642, 644 may be decoupled by pulling the ends 642, 644 apart, disengaging the projections 646.

Figure 15B:
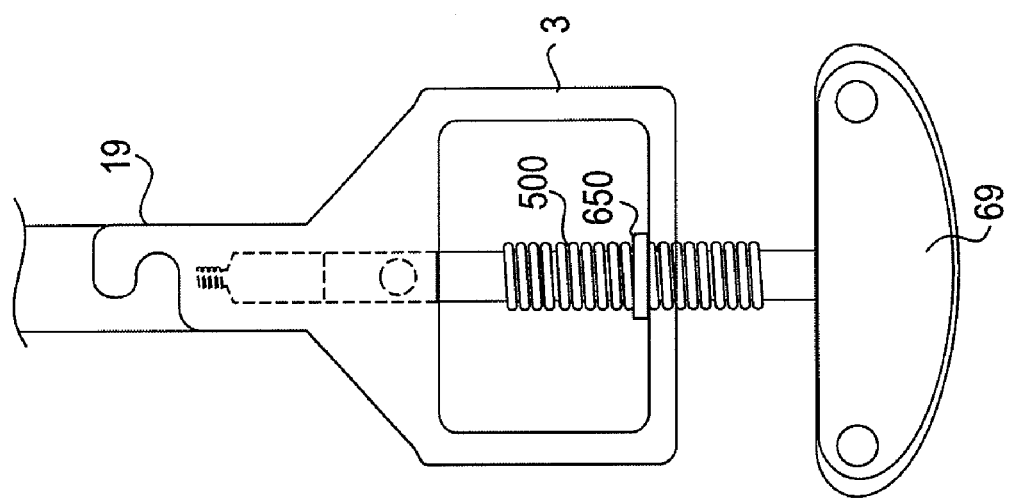
Figure 15A:
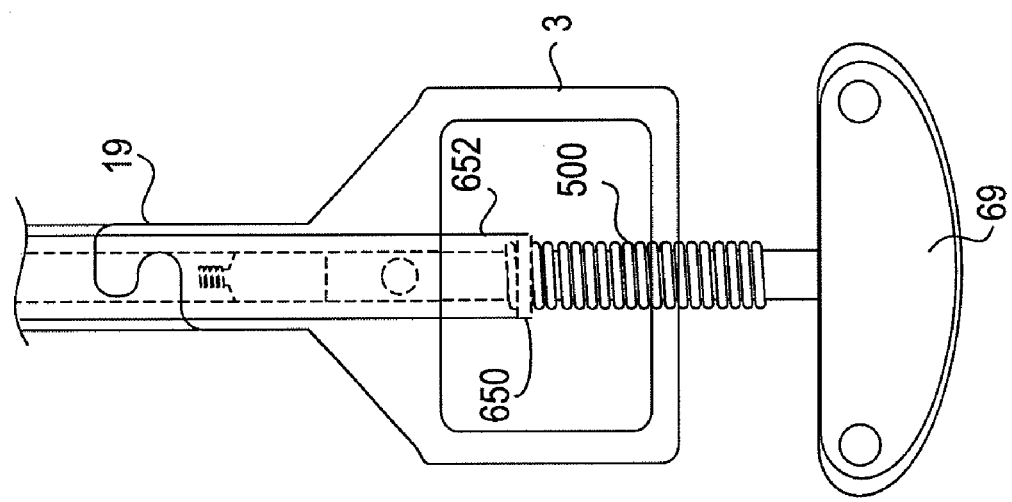

In a similar embodiment, illustrated in FIGS. 15A-15B, the interference element comprises a lock nut 650 which holds the stud 74 in place. FIG. 15A illustrates the stud 74 extending through housing 3 and holding the distal elements (not shown for clarity) in a desired position wherein the fixation device 14 is biased towards opening, i.e. the stud 74 is biased towards advancing. A lock nut 650 is screwed down over threads 500 by means of a torqueable sleeve 652 which is advanced over the stud 74. The torqueable sleeve 652 is joined with the lock nut 650 by any suitable means to provide torqueable attachment, such as projections into the lock nut 650, etc. The sleeve 652 is advanced until the lock nut 650 abuts the housing 3, as shown in FIG. 15B. Since the stud 74 is biased towards advancing, the lock nut 650 is held against the housing 3 preventing advancement of the stud 74 and hence locking the stud 74 in place. The sleeve 652 may then be removed and the fixation device 14 decoupled for implantation. It may be appreciated that the distal end 642 of the locking sheath 640 of FIGS. 14A-14D may also be considered a lock nut utilized in the same fashion. It may also be appreciated that the lock nut 650 may have external threads which mate with threads on housing 3. By screwing the lock nut 650 into the housing, the stud 74 may be prevent from advancing or retracting. Thus, such a locking feature may be used with fixation devices 14 which are not biased toward opening or closing.

Figure 16B:
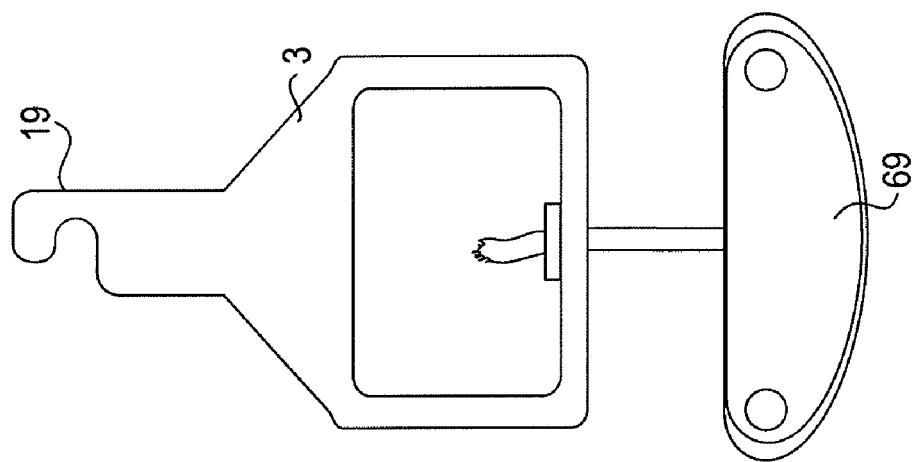
FIGS. 16A-16B illustrate a fixation device having a flexible line replacing the stud, and wherein the locking mechanism works against biasing forces that advance the flexible line.
Figure 16A:
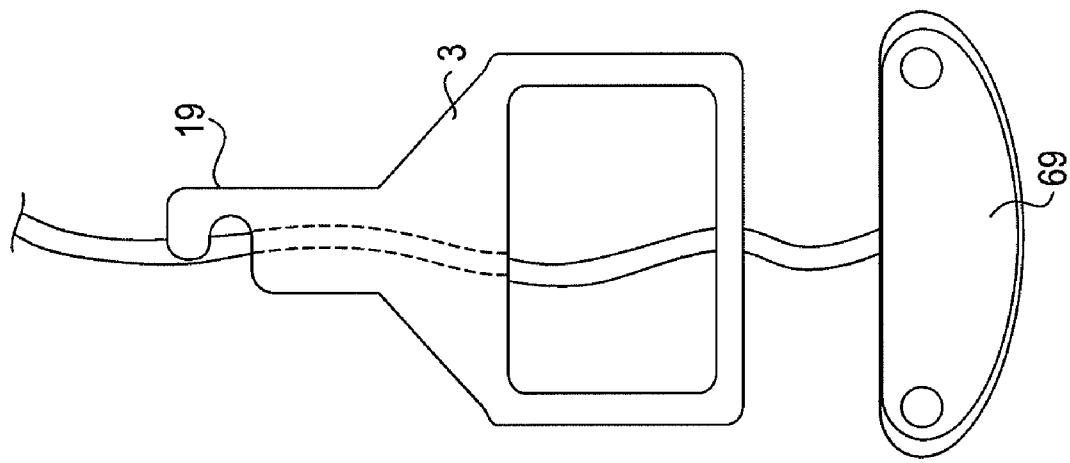

In another embodiment, illustrated in FIGS. 16A-16B, the stud comprises a suture line 75 or other flexible line. FIG. 16A illustrates the line 75 extending through housing 3 and allowing the distal elements (not shown for clarity) to move to a desired position wherein the fixation device 14 is biased towards opening, i.e. the line 75 is biased towards advancing. A suture fastener 698 is advanced down the line 75 until the fastener 698 abuts the housing 3 as shown in FIG. 16B. Since the line 75 is biased towards advancing, the fastener 698 is held against the housing 3 preventing advancement of the line 75 and hence locking the distal elements in place. The line 75 may then be cut proximal to the fastener 698 and the fixation device 14 decoupled for implantation.

Figure 17A:
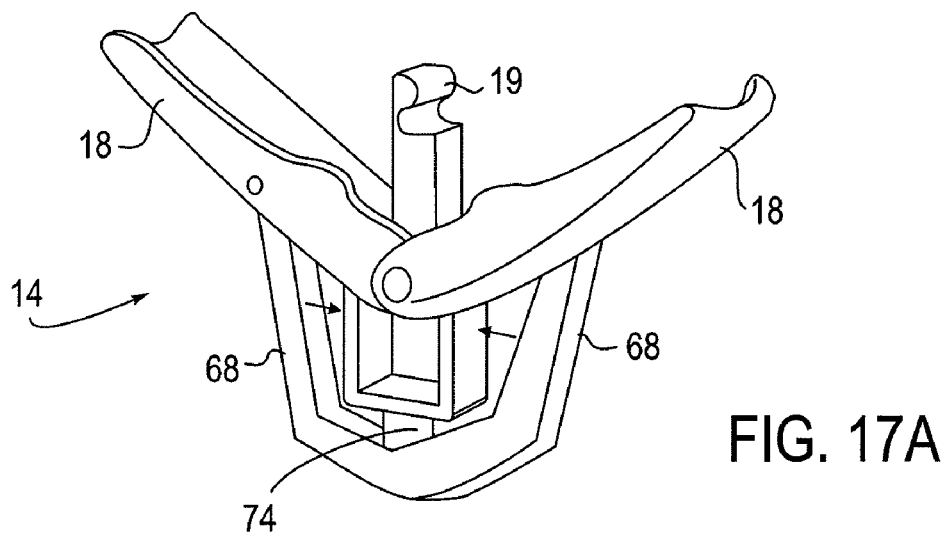
FIG. 17A illustrates an embodiment of a fixation device having legs spring biased toward a closed position.

As mentioned above, in many embodiments the distal elements 18 are pivotably coupled to the stud 74 by legs 68, whereby retracting the stud 74 pivots the distal elements 18 inwardly toward the closed position. In some embodiments, as illustrated in FIG. 17A, the legs 68 are spring biased toward the closed position. This may be achieved by forming the legs 68 from a continuous flexible material, such as cobalt chromium, stainless steel, Nitinol, Elgiloy® and the like. Opening of the distal elements 18 flexes the legs 68 outward, storing potential energy therein. Once the fixation device 14 has been desirably positioned, grasping tissue therebetween, the distal elements 18 are released and the legs 68 recoil toward the closed position, holding the distal elements 18 against the grasped tissue, thereby locking the distal elements 18 in place.

Figure 17B:
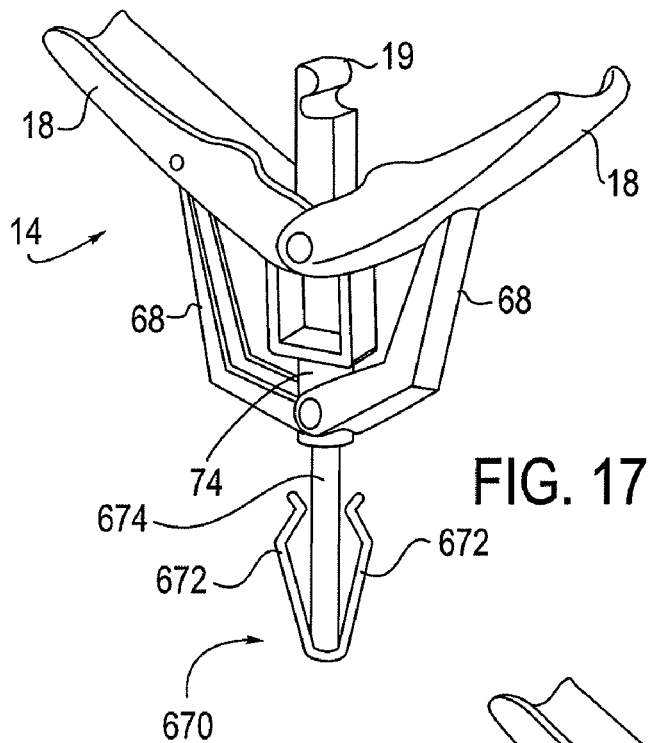
FIGS. 17B-17C illustrate the application of support sleeves to bias the distal elements of the fixation device toward a closed position.
Figure 17C:
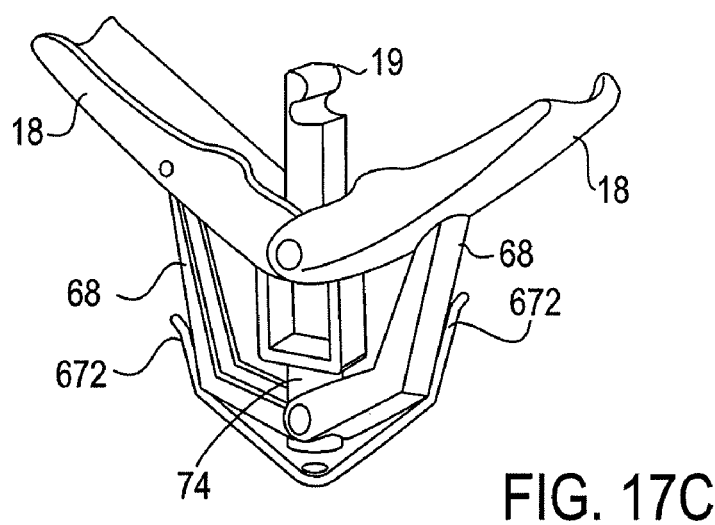

In other embodiments, the distal elements 18 are biased toward the closed position by the application of a biasing member. For example, as shown in FIGS. 17B-17C, the biasing member 670 may be comprised of a pair of support sleeves 672 mounted on a rod 674. The rod 674 may be advanced through the stud 74 so that the sleeves 672 are disposed distally of the fixation device 14. This allows the fixation device 14 to open, close, and/or invert as desired. Once the distal elements 18 have satisfactorily grasped the tissue, the distal elements 18 may be locked in place by retracing the rod 674 which slides the support sleeves 672 over the legs 68, as illustrated in FIG. 17C. The support sleeves 672 are comprised of a flexible material, such as cobalt chromium, stainless steel, Nitinol, Elgiloy® and the like, so that opening of the support sleeves 672 flexes the support sleeves 672 outward, spring loading the sleeves 672 and storing potential energy therein. The stored spring force then biases the sleeves 672 toward the closed position, holding the distal elements 18 against the grasped tissue, thereby locking the distal elements 18 in place.

Figure 18A:
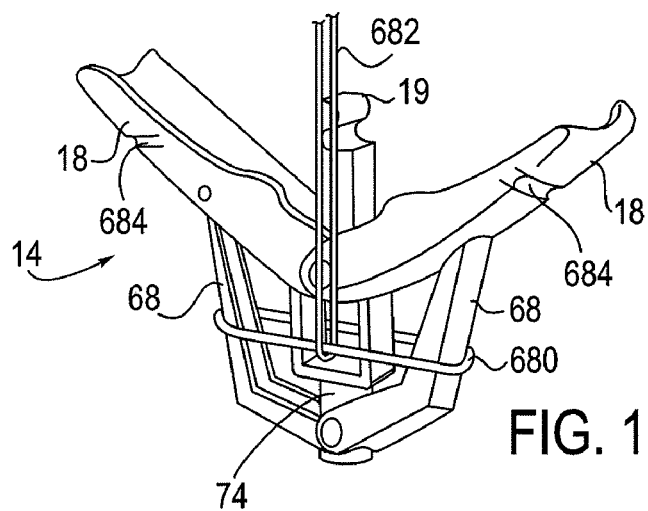
FIGS. 18A-18C illustrate an embodiment of a biasing member comprising a cinching band.
Figure 18B:
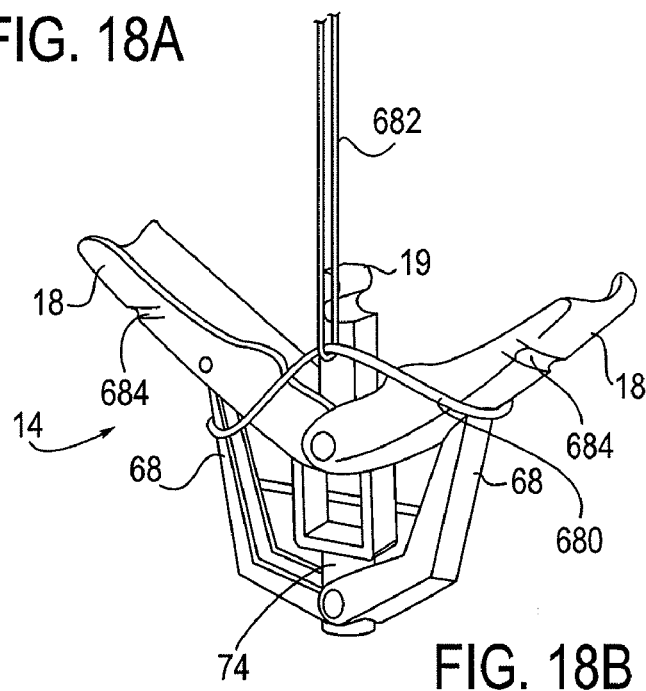
Figure 18C:
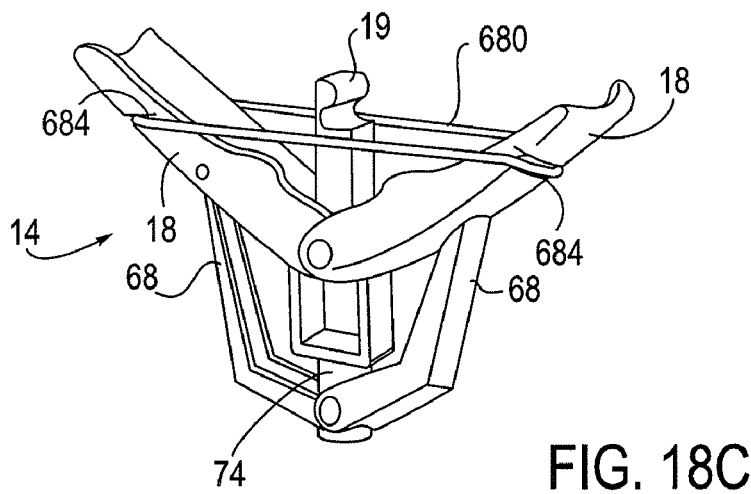

In other embodiments, the biasing member 670 comprises a cinching band. The cinching band may be elastic or substantially inelastic. An embodiment of an elastic cinching band 680 is illustrated in FIGS. 18A-18C. During positioning of the fixation device 14, the elastic cinching band 680 may be disposed distally of the distal elements 18, such as around the legs 68, as illustrated in FIG. 18A. This allows the distal elements 18 to be moved between open, closed and/or inverted positions as desired while grasping the tissue in a desired configuration. Once the tissue has been satisfactorily grasped, the distal elements 18 may be locked in place by repositioning of the band 680. The band 680 may be repositioned with the use of an adjustment line 682, such as a suture or wire, which is joined with the band 680. As illustrated in FIG. 18B, the band 680 may be pulled in the proximal direction by retracting the adjustment line 682. This draws the band 680 over the distal elements 18 in a stretched configuration, as illustrated in FIG. 18C. Stretching of the elastic cinching band 680 stores potential energy therein. The stored spring force then biases the distal elements 18 toward the closed position, holding the distal elements 18 against the grasped tissue, thereby locking the distal elements 18 in place. The distal elements 18 may also include grooves 684 into which the band 680 may be placed. Such grooves 684 may reduce possible slippage of the band 680 and indicate to the user a desired position along the distal elements 18 for placement. The adjustment line 682 is then removed and the fixation device 14 left in place. It may be appreciated that an inelastic cinching band would function similarly. One difference is that the inelastic band may hang loosely around the legs 68 and would be taut when positioned around the distal elements 18. The distal elements 18 are locked at a position based on the length of the inelastic cinching band whereas the distal elements 18 would be held a position based on the stored potential energy of the elastic cinching band.

Figure 19A:
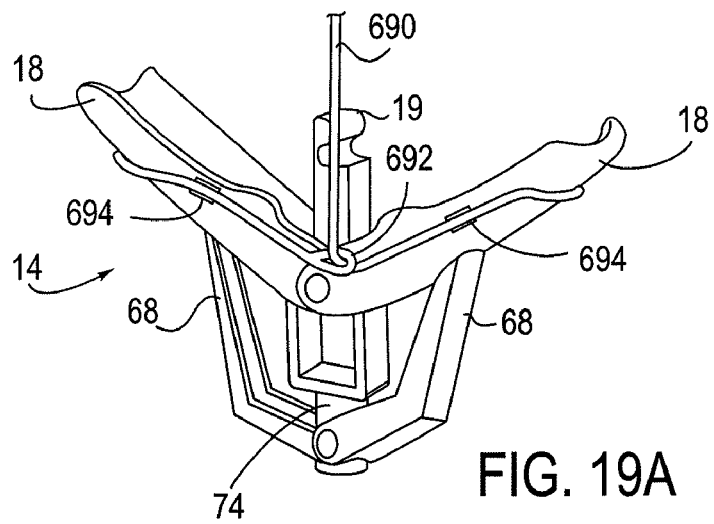
FIGS. 19A-19C illustrate an embodiment of a biasing member comprising a cinching line.
Figure 19B:
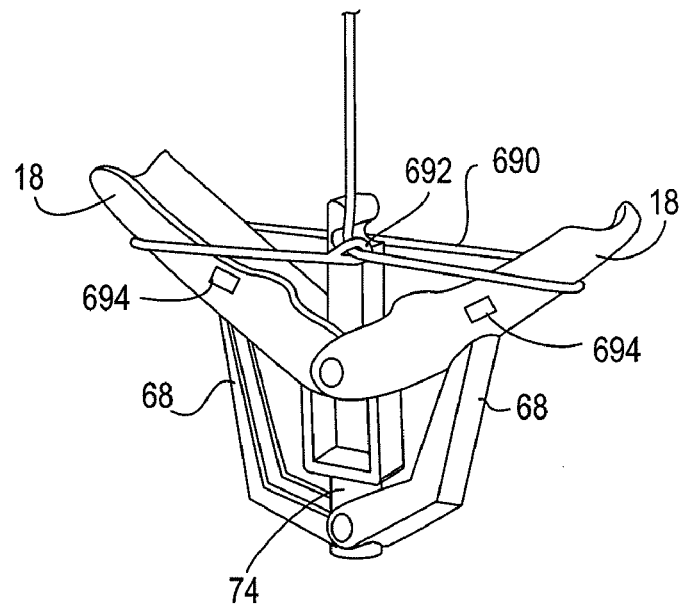
Figure 19C:
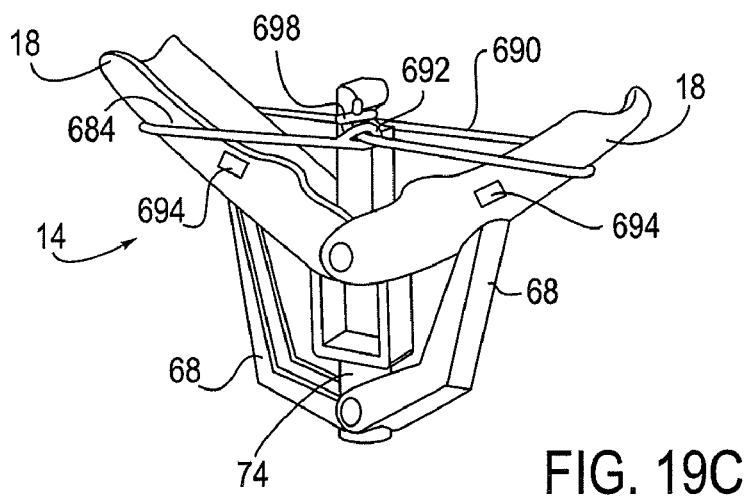

In other embodiments, the cinching band comprises a cinching line 690, as illustrated in FIGS. 19A-19C. The cinching line 690 is typically comprised of a substantially inelastic material, such as a suture, thread or filament. The cinching line 690 is wrapped around the fixation device 14 in a "lasso"-type configuration. Typically, the cinching line 690 has a loop 692 at one end through which the line 690 passes so that pulling on the line 690 tightens the lasso. In one embodiment, illustrated in FIG. 19A, the cinching line 690 is wrapped loosely around the distal elements 18. This allows the distal elements 18 to be moved between open, closed and/or inverted positions as desired while grasping the tissue in a desired configuration. The line 690 may be adhered to the distal elements 18 (or other parts of the fixation device) at various locations 694 to assist in keeping the line 690 in place. Once the tissue has been satisfactorily grasped, the distal elements 18 may be locked in place by tightening the cinching line 690. The cinching line 690 may be tightened by pulling the line 690 in the proximal direction so the lasso tightens around the distal elements 18, as illustrated in FIG. 19B. Such tightening allows the line 690 to break from the adhered locations 694. The cinching line 690 biases the distal elements 18 toward the closed position, holding the distal elements 18 against the grasped tissue, thereby locking the distal elements 18 in place. The distal elements 18 may be held at any desired position by applying more or less force to the cinching line 690. It may be appreciated that the distal elements 18 may also include grooves into which the line 690 may be placed. Such grooves may reduce possible slippage of the line 690 and indicate to the user a desired position along the distal elements 18 for placement. Referring to FIG. 19C, a suture fastener 698 is then advanced along the cinching line 690 and positioned against the loop 692 to hold the line 690 in place. The line 690 is then cut proximal to the suture fastener 698 and the fixation device 14 left in place.

Figure 20:
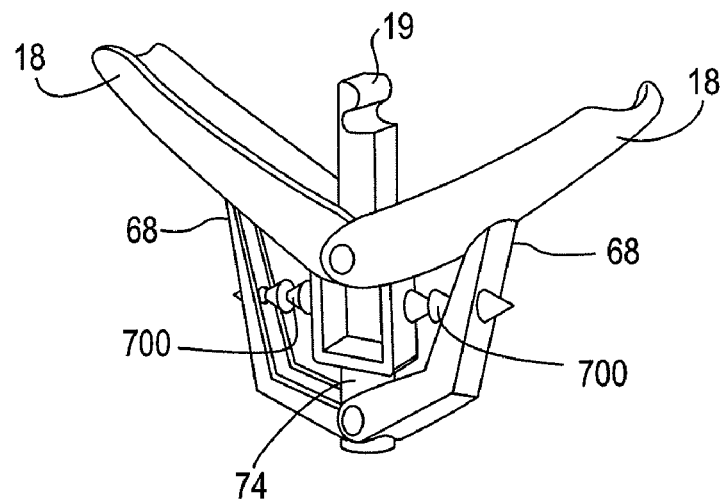
FIG. 20 illustrates a locking mechanism comprising barbs which attach to the legs, holding the legs in a fixed position.
Figure 21A:
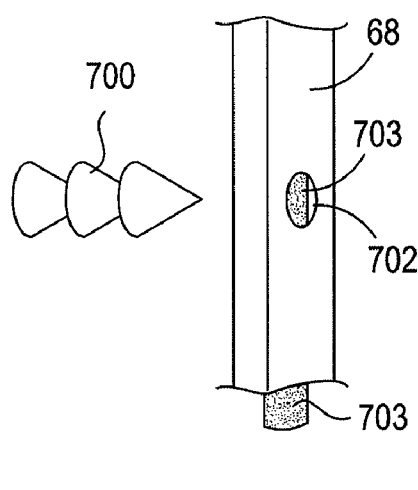
FIGS. 21A-21C illustrate attachment of the barbs to the legs.
Figure 21B:
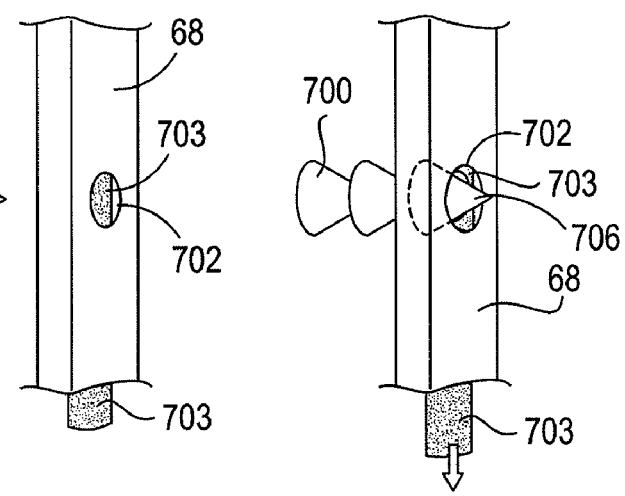
Figure 21C:
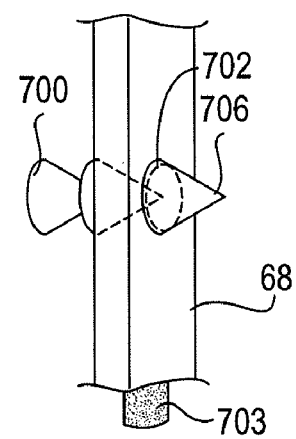

In some embodiments, the locking mechanism is comprised of structures, such as barbs, which attach to the legs, holding the legs in a fixed position. FIG. 20 illustrates an embodiment of such a locking mechanism. Here, barbs 700 extend outwardly from the housing 3 toward the legs 68. The barbs 700 are segmented so that the barbs 700 can be extended through the legs 68 to variable extents which in turn allows the distal elements 18 to be locked at various positions. FIGS. 21A-21C illustrate such attachment to the legs 68. FIG. 21A illustrates a barb 700 approaching a leg 68. The leg 68 has a hole 702 which is covered by a flap 703. As the distal element 18 rotates toward the closed position, the leg 68 is drawn toward the barb 700. Referring to FIG. 21B, the barb 700 then advances through the hole 702, pushing the flap 703 open. FIG. 21C illustrates a first segment 706 of the barb 700 extending through the hole 702 wherein the flap 703 recoils and wedges against the barb 700. This holds the barb 700 in attachment with the leg 68. The leg 68 is now locked in place, thereby locking the associated distal element 18 in place. Additional segments of the barb 700 may be advanced through the leg 68 to lock the distal elements 18 in more closed positions. It may also be appreciated that the barb 700 may only include a first segment 706 wherein the leg 68 may be locked in a single position, rather than allowing variable positions.

It is further within the scope of the present invention that the locking mechanism be a wedge contacting a sloped surface, a threaded engagement, a spring, a groove engaging protrusion, a ratchet mechanism, a pin engaging a hole, a magnet attracting to a dipole magnet, a geared mechanism pulley or belt mechanism and the like. Further, the lock mechanism may include use of epoxy resin, energy (such as radiofrequency or ultrasonic welding) to bind the stud relative to the housing.

It may be appreciated that the locking mechanisms of the present invention may be utilized in a variety of fixation devices having any number and combination of proximal and/or distal elements. For example, the locking mechanisms may be used in combination with a device having a single distal element or a single pair comprising one proximal element and one distal element wherein a leaflet or other tissue is grasped between the proximal and distal element of the pair. In another example, the locking mechanisms may be used in combination with a device having multiple distal elements, such as three distal elements. In general, the locking mechanisms of the present invention may be used to lock any moveable elements in place.

It may further be appreciated that the locking mechanism of the present invention may also be utilized in other devices and systems, such as to lock catheters, retractors, or other medical instruments such as graspers or biopsy forceps in a particular position prior to, during, or following a medical procedure. Examples of catheters include steerable guide catheters, such as described in U.S. patent Ser. No. 10/441,753 incorporated herein by reference, and inner and/or outer guide catheters, such as described in U.S. patent Ser. No. 10/441,531 incorporated herein by reference. In these examples, the locking mechanism of the present invention function as the locking actuators.

Figure 22:
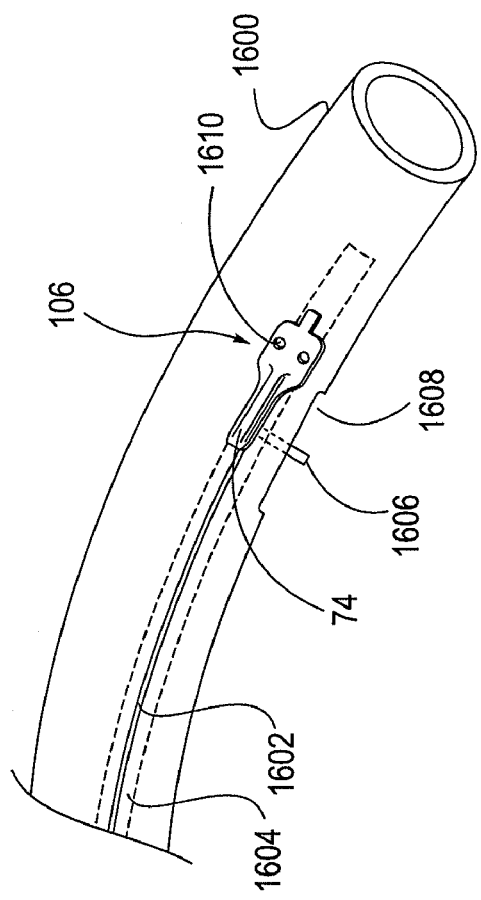
FIG. 22 illustrates a catheter having an embodiment of a locking mechanism of the present invention.

FIG. 22 illustrates a proximal end of a catheter 1600 having an embodiment of a locking mechanism 106 of the present invention. Here, the stud 74 is fixedly attached to a pullwire 1602 which extends along the catheter 1600, typically within a lumen 1604 in the wall of the catheter 1600. In this embodiment, a knob 1606 is connected with the stud 74 and extends radially outwardly through an opening 1608 in the catheter 1600. The opening 1608 is shaped to allow axial movement of the knob 1606 along the length of a portion of the proximal end of the catheter 1600. Axial movement of the knob 1606 in turn moves the stud 74 and attached pullwire 1602 which in turn steers the catheter 1600. The pullwire 1602 can be locked in any desired axial position by the locking mechanism 106.

The locking mechanism includes one or more wedging elements 1610 which wedge against the stud 74 to hold the stud 74 and attached pullwire 1602 in a desired axial position. FIG. 22 illustrates the locking mechanism of FIGS. 4A-4C, however it may be appreciated that any of the locking mechanism disclosed herein may be used. When in the unlocked position, the stud 74 is free to move. When in the locked position, a spring forces the wedging elements 1610 downwards and wedges the wedging elements 1610 between a sloping surface and the stud 74. This restricts motion of the stud 74, which in turn locks the pullwire 1602 in place.

Figure 23:
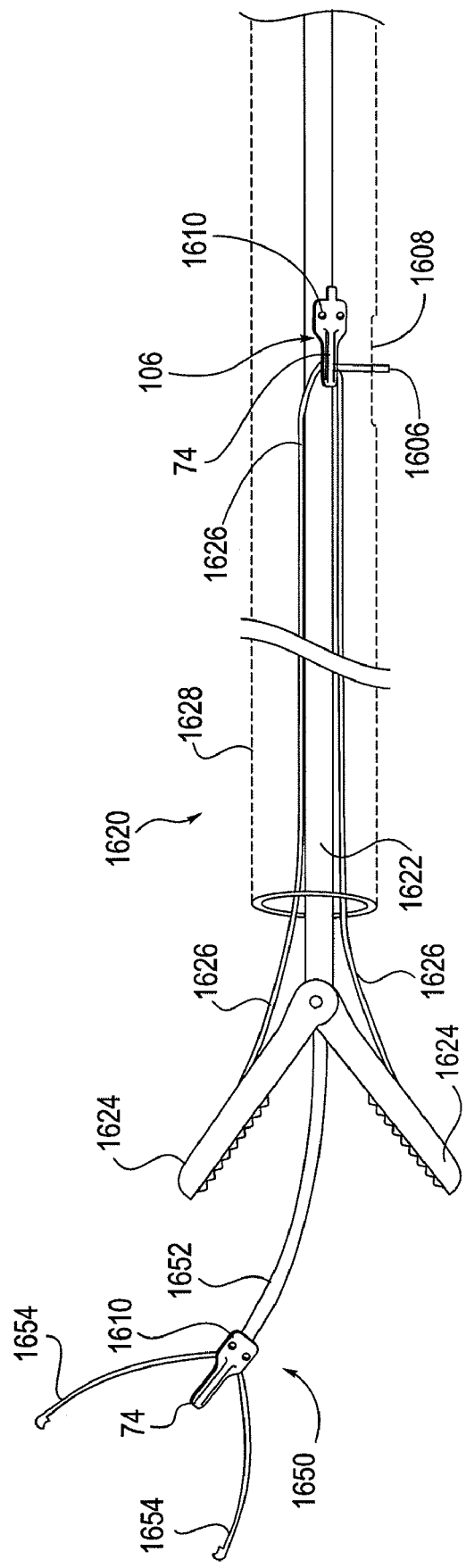
FIG. 23 illustrates a grasper having an embodiment of a locking mechanism of the present invention.

FIG. 23 illustrates an endoscopic grasper 1620 having an embodiment of a locking mechanism 106 of the present invention. The grasper 1620 comprises an elongate shaft 1622 rotateably coupled at its distal end with a pair of jaws 1624. The jaws 1624 are spring loaded so that the jaws 1624 are in a closed position unless tension is applied to a pair of pullwires 1626 which draw the jaws 1624 toward an open position. The shaft 1622 and pullwires 1626 extend through a tubular sheath 1628 as shown. The jaws 1624 may be locked in any position including the closed position, a fully open position and any position therebetween. This may be achieved with a locking mechanism 106 of the present invention. Here, the stud 74 is fixedly attached to the pullwires 1626 which extend along the shaft 1622 to the proximal end of the sheath 1628. In this embodiment, a knob 1606 is connected with the stud 74 and extends radially outwardly through an opening 1608 in the sheath 1628. The opening 1608 is shaped to allow axial movement of the knob 1606 along the length of a portion of the proximal end of the sheath 1628. Axial movement of the knob 1606 in turn moves the stud 74 and attached pullwires 1626 which in turn steers the catheter 1600. The pullwire 1602 can be locked in any desired axial position by the locking mechanism 106. The locking mechanism includes one or more wedging elements 1610 which wedge against the stud 74 to hold the stud 74 and attached pullwires 1626 in a desired axial position.

FIG. 23 also illustrates an additional grasper 1650 advanceable through a lumen in the shaft 1622 of the endoscopic grasper 1620. Here, the additional grasper 1650 has an elongate shaft 1652 coupled with a stud 74 of a locking mechanism 1610. Advancement and retraction of the stud 74 opens and closes a pair of jaws 1654 so that the jaws 1654 are moveable in a manner similar to the distal elements of the above described fixation devices. Thus, the jaws 1654 may be locked in place by the locking mechanism 1610 as described above. It may be appreciated that the jaws 1624 of the endoscopic grasper 1620 may be locked in this manner as an alternative to the locking mechanism disposed near its distal end.

FIG. 23 illustrates the locking mechanism of FIGS. 4A-4C, however it may be appreciated that any of the locking mechanism disclosed herein may be used. When in the unlocked position, the stud 74 is free to move. When in the locked position, a spring forces the wedging elements 1610 downwards and wedges the wedging elements 1610 between a sloping surface and the stud 74. This restricts motion of the stud 74, which in turn locks the pullwire 1602 in place.

It may be appreciated that locking mechanisms of the present invention may be disposed within or near a distal portion of a device where space is limited, along an elongate portion of the device (particularly if multiple locking mechanisms are desired), or within or near a proximal end of the device (such as illustrated in FIGS. 22-23). Multiple locking mechanisms may be desired when multiple pullwires are used to steer a sheath or catheter. Thus, the multiple locking mechanisms can assist in positioning instruments in tortuous body paths or locations.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. An implantable fixation device for engaging cardiac tissue, said device comprising:
    a pair of elements each having a first end, a free end opposite the first end, and an engagement surface therebetween for engaging the tissue, the first ends being movable between an open position wherein the free ends are spaced apart and a closed position wherein the free ends are closer together with the engagement surfaces generally facing each other, wherein in the closed position the pair of elements is adapted to reduce retrograde blood flow across the engaged tissue;
    a moveable stud coupled to the pair of elements wherein movement of the stud moves the elements between the open and the closed positions; and
    a locking mechanism coupled to the elements for locking the elements in place, wherein the locking mechanism comprises an engagement element engageable with the moveable stud so as to restrict movement of the stud, the engagement element having at least one protrusion which mates with at least one external groove on the stud so as to restrict movement of the stud.

2. A fixation device as in claim 1, wherein the moveable stud comprises a flexible line.

3. A fixation device as in claim 2, wherein the locking mechanism comprises an interference element which is positionable along the flexible line so that the interference element prevents movement of the flexible line in at least a first direction by contacting a stationary surface of the fixation device.

4. A fixation device as in claim 1, wherein the locking mechanism comprises gears, wherein movement of the gears moves the elements between the positions while locking the elements in place at each position.

5. A fixation device as in claim 1, wherein the locking mechanism comprises a biasing member which biases the elements toward one of the positions.

6. A fixation device as in claim 5, wherein the biasing member comprises a pair of spring loaded support sleeves positionable against a portion of the fixation device so as to bias the elements toward one of the positions.

7. A fixation device as in claim 5, wherein the biasing member comprises a cinching band positionable around the elements so as to bias the elements toward one of the positions.

8. A fixation device as in claim 7, wherein the cinching band comprises an elastic cinching band positionable around the elements in a stretched configuration so as to apply biasing force to the elements.

9. A fixation device as in claim 7, wherein the cinching band comprises a cinching line positionable around the elements in a lasso configuration so as to apply biasing force to the elements when tightened.

10. A fixation device as in claim 1, further comprising at least one leg joined with the elements so that movement of the at least one leg moves the elements between the positions.

11. A fixation device as in claim 10, wherein the at least one leg has a spring loaded configuration so as to bias the elements toward one of the positions.

12. A fixation device as in claim 10, wherein the locking mechanism comprises a structure joinable with the at least one leg so as to prevent movement of the elements.

13. A fixation device as in claim 12, wherein the structure comprises a barb advanceable through the at least one leg.

14. A fixation device as in claim 1, further comprising an unlocking mechanism for disengaging the locking mechanism.

15. An implantable locking mechanism for fixing cardiac tissue, said mechanism comprising:
- a moveable stud coupled to a device, wherein movement of the stud actuates movement of a portion of a device to a desired position in a range from a first position to a second position, wherein in the desired position the device is adapted to reduce retrograde blood flow across the fixed cardiac tissue;
- at least one element configured to engage the stud to restrict movement of the stud which locks the device in the desired position, wherein the at least one element comprises at least one cam, the at least one cam pivotable to frictionally engage the stud to restrict movement thereof; and
- an unlocking mechanism configured to disengage the at least one element from the stud which allows movement of the stud.

16. A locking mechanism as in claim 15, wherein the at least one element comprises a binding plate having a first end, a second end and a portion therebetween shaped to at least partially surround the stud, the binding plate positioned so that the portion at least partially surrounds the stud.

17. A locking mechanism as in claim 16, wherein the portion shaped to at least partially surround the stud comprises an aperture, the binding plate positioned so that the stud passes through the aperture.

18. A locking mechanism as in claim 17, further comprising a spring configured to force the aperture against the stud to restrict movement of the stud through the aperture.

19. A locking mechanism as in claim 16, wherein the unlocking mechanism comprises a harness, the harness adapted to move the second end while the first end remains substantially stationary so as to reduce frictional engagement of the at least partially surrounding portion with the stud.

20. A locking mechanism as in claim 15, wherein the at least one cam has an inward surface engageable with the stud and an outward surface connected with a spring which forces the inward surface against the stud to restrict movement of the stud.

21. A locking mechanism as in claim 15, wherein the stud has at least one external groove for engagement with the at least one element to restrict movement of the stud.

22. A locking mechanism as in claim 21, wherein the at least one element comprises at least one protrusion which mates with the at least one external groove of the stud wherein the at least one element is moveable to engage the at least one protrusion with the at least one external groove of the stud to restrict movement of the stud.

23. A locking mechanism as in claim 22, wherein the unlocking mechanism comprises a hinge component which moves the at least one element to disengage the at least one protrusion from the at least one external groove.

24. A locking mechanism as in claim 22, wherein the at least one external groove comprises threads and the at least one element comprises a split nut.

* * * * *